US008470791B2

(12) United States Patent
Hansen et al.

(10) Patent No.: US 8,470,791 B2
(45) Date of Patent: Jun. 25, 2013

(54) RNA ANTAGONIST COMPOUNDS FOR THE INHIBITION OF APO-B100 EXPRESSION

(75) Inventors: Henrik Frydenlund Hansen, Rødovre (DK); Jens Bo Rode Hansen, Charlottenlund (DK); Christoph Rosenbohm, Birkerød (DK); Ellen Marie Straarup, Birkerød (DK)

(73) Assignee: Santaris Pharma A/S, Hoersholm (DK)

( * ) Notice: Subject to any disclaimer, the term of this patent is extended or adjusted under 35 U.S.C. 154(b) by 346 days.

(21) Appl. No.: 12/532,275

(22) PCT Filed: Mar. 19, 2008

(86) PCT No.: PCT/EP2008/053309
§ 371 (c)(1),
(2), (4) Date: Mar. 22, 2010

(87) PCT Pub. No.: WO2008/113830
PCT Pub. Date: Sep. 25, 2008

(65) Prior Publication Data
US 2010/0227914 A1  Sep. 9, 2010

Related U.S. Application Data

(60) Provisional application No. 60/896,419, filed on Mar. 22, 2007, provisional application No. 60/977,409, filed on Oct. 4, 2007.

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl.
USPC ....... 514/44 A; 536/23.1; 536/24.1; 536/24.5; 435/375; 435/377

(58) Field of Classification Search
None
See application file for complete search history.

(56) References Cited

U.S. PATENT DOCUMENTS

| 4,914,210 | A | 4/1990 | Levenson et al. |
| 4,962,029 | A | 10/1990 | Levenson et al. |
| 5,919,795 | A | 7/1999 | Chang et al. |
| 6,030,785 | A | 2/2000 | Katze et al. |
| 6,121,283 | A | 9/2000 | Chang et al. |
| 6,284,458 | B1 | 9/2001 | Anderson et al. |
| 6,423,489 | B1 | 7/2002 | Anderson et al. |
| 6,433,159 | B1 | 8/2002 | Anderson et al. |
| 7,087,229 | B2 | 8/2006 | Zhao et al. |
| 2005/0069522 | A1 | 3/2005 | Colonno et al. |
| 2005/0261218 | A1 | 11/2005 | Esau et al. |
| 2006/0035212 | A1 | 2/2006 | Balakireva |
| 2006/0035858 | A1 | 2/2006 | Geary et al. |
| 2006/0040989 | A1 | 2/2006 | Meerpoel et al. |
| 2006/0185027 | A1 | 8/2006 | Bartel et al. |
| 2009/0306180 | A1* | 12/2009 | Bhanot et al. ............... 514/44 A |

FOREIGN PATENT DOCUMENTS

| EP | 0 699 751 A1 | 3/1996 |
| EP | 1 099 442 A2 | 5/2001 |
| EP | 0 662 157 B1 | 6/2001 |
| EP | 1 222 309 B1 | 7/2005 |
| WO | WO 95/30746 A1 | 11/1995 |
| WO | WO 99/14226 A2 | 3/1999 |
| WO | WO 00/56746 A2 | 9/2000 |
| WO | WO 00/56748 A1 | 9/2000 |
| WO | WO 00/66604 A2 | 11/2000 |
| WO | WO 01/23613 A1 | 4/2001 |
| WO | WO 01/25248 A2 | 4/2001 |
| WO | WO 02/28875 A2 | 4/2002 |
| WO | WO 02/094250 A2 | 11/2002 |
| WO | WO 03/006475 A2 | 1/2003 |
| WO | WO 03/011887 A2 | 2/2003 |
| WO | WO 03/095467 A1 | 11/2003 |
| WO | WO 2004/044181 A2 | 5/2004 |
| WO | WO 2004/046160 A2 | 6/2004 |
| WO | WO 2004/069991 A2 | 8/2004 |
| WO | WO 2004/091515 A2 | 10/2004 |
| WO | WO 2005/013901 A2 | 2/2005 |
| WO | WO 2005/054494 A2 | 6/2005 |
| WO | WO 2005/058824 A2 | 6/2005 |
| WO | WO 2005/061710 A1 | 7/2005 |
| WO | WO 2005/098029 A2 | 10/2005 |
| WO | WO 2005/107816 A2 | 11/2005 |
| WO | WO 2006/010423 A2 | 2/2006 |
| WO | WO 2006/020676 A2 | 2/2006 |
| WO | WO 2006/020768 A2 | 2/2006 |
| WO | WO 2006/036916 A2 | 4/2006 |
| WO | WO 2006/053430 A1 | 5/2006 |
| WO | WO 2006/093526 A2 | 9/2006 |
| WO | WO 2006/112872 A2 | 10/2006 |

(Continued)

OTHER PUBLICATIONS

Beaucage, L. and Iyer, R., "Advances in the Synthesis of Oligonucleotides by the Phosphoramidite Approach," *Tetrahedron* 48:2223-2311, Pergamon Press, United Kingdom (1992).

Beaucage, L. and Iyer, R., "The Synthesis of Modified Oligonucleotides by the Phosphoramidite Approach and Their Applications," *Tetrahedron* 49:6123-6194, Pergamon Press, United Kingdom (1993).

Braasch, D., et al., "Antisense inhibition of gene expression in cells by oligonucleotides incorporating locked nucleic acids: effect of mRNA target sequence and chimera design," *Nucleic Acids Res.* 30:5160-5167, Oxford University Press, United Kingdom (2002).

Christensen, U. And Pedersen, E., "Intercalating nucleic acids containing insertions of 1-O-(1-pyrenylmethyl)glycerol: stabilisation of dsDNA and discrimination of DNA over RNA," *Nucleic Acids Res.* 30:4918-4925, Oxford University Press, United Kingdom (2002).

(Continued)

*Primary Examiner* — Sean McGarry
(74) *Attorney, Agent, or Firm* — Fish & Richardson P.C.

(57) ABSTRACT

Short oligonucleotides directed against the Apo-B100 gene are provided for modulating the expression of Apo-B100. Methods of using these compounds for modulation of Apo-B100 expression and for the treatment of diseases associated with Apo-B100 expression are provided. The oligonucleotides comprise deoxyribonucleosides and locked nucleic acids.

28 Claims, 7 Drawing Sheets

FOREIGN PATENT DOCUMENTS

| | | |
|---|---|---|
| WO | WO 2006/113910 A2 | 10/2006 |
| WO | WO 2007/031081 A2 | 3/2007 |
| WO | WO 2007/031091 A2 | 3/2007 |
| WO | WO 2007/112753 A2 | 10/2007 |
| WO | WO 2007/112754 A2 | 10/2007 |
| WO | WO 2007/134181 A2 | 11/2007 |
| WO | WO 2008/034122 A2 | 3/2008 |
| WO | WO 2008/034123 A2 | 3/2008 |
| WO | WO 2008/043753 A2 | 4/2008 |
| WO | WO 2008/061537 A2 | 5/2008 |
| WO | WO 2008/089767 A1 | 7/2008 |
| WO | WO 2008/124384 A2 | 10/2008 |
| WO | WO 2008/150729 A2 | 12/2008 |
| WO | WO 2008/154401 A2 | 12/2008 |
| WO | WO 2009/020771 A2 | 2/2009 |

OTHER PUBLICATIONS

Crooke, R., et al., "An apolipoprotein B antisense oligonucleotide lowers LDL cholesterol in hyperlipidemic mice without causing hepatic steatosis," *J. Lipid Res.* 46:872-884, American Society for Biochemistry and Molecular Biology, Inc., United States (2005).

Crooke, R., "Chapter 3: In Vitro Cellular Uptake, Distribution, and Metabolism of Oligonucleotides," in *Antisense Research and Application* 131:103-140, Springer-Verlag, Germany (1998).

Dass, C., "Vehicles for oligonucleotide delivery to tumours," *J. Pharm. Pharmacol.* 54:3-27, Pharmaceutical Press, United Kingdom (2002).

Davidson, N. and Shelness, G., "Apolipoprotein B: mRNA Editing, Lipoprotein Assembly, and Presecretory Degradation," *Annu. Rev. Nutr.* 20:169-193, Annual Reviews, United States (2000).

Davis, S., et al., "Improved targeting of miRNA with antisense oligonucleotides," *Nucleic Acids Res.* 34:2294-2304, Oxford University Press, United Kingdom (2006).

Deere, J., et al., "Antisense Prosphorodiamidate Morpholino Oligomer Length and Target Position Effects on Gene-Specific Inhibition in *Eschericia coli*," *Antimicrobial Agents and Chemotherapy* 49:249-255, American Society for Microbiology, United States (2005).

Elbashir, S., et al., "Analysis of gene function in somatic mammalian cells using small interfering RNAs," *Methods* 26:199-213, Academic Press, United States (2002).

Elmén, J., et al., "Locked nucleic acid containing antisense oligonucleotides enhance inhibition of HIV-1 genome dimerization and inhibit virus replication," *FEBS Letters* 578:285-290, Elsevier B.V., The Netherlands (2004).

Feld, J., et al., "Ribavirin Improves Early Response to Peginterferon Through Improved Interferon Signaling," *Gastroenterology* 139:154-162, W.B. Saunders, United States (2010).

Freier, S. And Altmann, K.-H., "The ups and downs of nucleic acid duplex stability: structure—stability studies on chemically-modified DNA: RNA duplexes," *Nucleic Acids Res.* 25:4429-4443, Oxford University Press, United Kingdom (1997).

Frieden, M., et al., "Expanding the design horizon of antisense oligonucleotides with alpha-L-LNA," *Nucleic Acids Res.* 31:6365-6372, Oxford University Press, United Kingdom (2003).

Gentleman, R., et al., "Bioconductor: open software development for computational biology and bioinformatics," *Genome Biol* 5:R80, BioMed Central Ltd., United Kingdom (2004).

Giles, R., et al., "Selecting optimal oligonucleotide composition for maximal antisense effect following streptolysin O-mediated delivery into human leukaemia cells," *Nucleic Acid Res.* 26:1567-1575, Oxford University Press, United Kingdom (1998).

Greene, T. And Wuts, P., Protective Groups in Organic Synthesis, [Table of Contents], 3rd ed., John Wiley & Sons, Chichester, England (1999).

Grünweller, A., et al., "Comparison of different antisense strategies in mammalian cells using locked nucleic acids, 2'-O-methyl RNA, phosphorothioates and small interfering RNA," *Nucleic Acids Res.* 31:3185-3195, Oxford University Press, United Kingdom (2003).

Hanecak, R., et al., "Antisense Oligonucleotide Inhibition of Hepatitis C Virus Gene Expression in Transformed Hepatocytes," *J. Virol.* 70:5203-5212, American Society for Microbiology, United States (1996).

Hu, Q., "Subcellular trafficking of antisesnse oligonucleotides and down-regulation of bcl-2 gene expression in human melanoma cells using a fusogenic liposome delivery system," *Nucleic Acid Res.* 30:3632-3641, Oxford University Press, United Kingdom (2002).

Huang, H., et al., "Hepatitis C virus production by human hepatocytes dependent on assembly and secretion of very low-density lipoproteins," *Proc. Natl. Acad. Sci. U.S.A.* 104:5848-5853, National Academy of Sciences, United States (2007).

Huber, W., et al., "Variance stabilization applied to microarray data calibration and to the quantification of differential expression," *Bioinformatics* 18:S96-S104, Oxford University Press, United Kingdom (2002).

Hutton, J., "Renaturation kinetics and thermal stability of DNA in aqueous solutions of formamide and urea," *Nucleic Acids Res.* 4:3537-3555, Oxford University Press, United Kingdom (1977).

Hutvágner, G., et al., "A Cellular Function for the RNA-Interference Enzyme Dicer in the Maturation of the *let-7* Small Temporal RNA," *Science* 293:834-838, American Assn. for the Advancement of Science, United States (2001).

Hutvágner, G., et al., "Sequence-Specific Inhibition of Small RNA Function," *PLoS Biology* 2:0465-0475, Public Library of Science, United States (2004).

Ittig, D., et al., "Nuclear antisense effects in cyclophilin a pre-mRNA splicing by oligonucleotides: a comparison of tricyclo-DNA with LNA," *Nucleic Acids Res.* 32:346-353, Oxford University Press (2004).

Jepsen, J., et al., "Locked Nucleic Acid: A Potent Nucleic Acid Analog in Therapeutics and Biotechnology," *Oligonucleotides* 14:130-146, Mary Ann Liebert, Inc., United States (2004).

Johansson, H., et al., "Target-specific arrest of mRNA translation by antisense 2'-O-alkyloligonucleotides," *Nucleic Acids Res.* 22: 4591-4598, Oxford University Press, United Kingdom (1994).

Johnson, S., et al., "RAS is Regulated by the let-7 MicroRNA Family," *Cell* 120:635-647, Cell Press, United States (2005).

Kauppinen, S., et aL, "Locked nucleic acid (LNA): High affinity targeting of RNA for diagnostics and therapeutics," *Drug Discovery Today: Technologies* 2:287-290, Elsevier, Ltd., The Netherlands (2005).

Ketting, R., et al., "Dicer functions in RNA interference and in synthesis of small RNA involved in developmental timing in *C.elegans*," *Genes Dev.* 15:2654-2659, Cold Spring Harbor Laboratory Press, United States (2001).

Khoo, B., et al, "Antisense oligonucleotide-induced alternative splicing of the APOB mRNA generates a novel isoform of APOB," *BMC Mol. Biol.* 8:3, BioMed Central, United Kingdom (2007).

Kloosterman, W., et al., "Substrate requirements for *let-7* function in the developing zebrafish embryo," *Nucleic Acids Res.* 32:6284-6291, Oxford University Press, United Kingdom (2004).

Krukemeyer, M., et al., "Description of B lymphocytes and plasma cells, complement, and chemokines/receptors in acute liver allograft rejection," *Transplantation* 78:65-70, Lippincott Williams & Wilkins, United States (2004).

Krützfeldt, J., et al., Specificity, duplex degradation and subcellular localization of antagomirs, *Nucleic Acids Res.* 35:2885-2892, Oxford University Press, United Kingdom (2007).

Kurreck, J., et aL, "Design of antisense oligonucleotides stabilized by locked nucleic acids," *Nucleic Acids Res.* 30:1911-1918, Oxford University Press, United Kingdom (2002).

Lanford, R., et al., "Antiviral Effect and Virus-Host Interactions in Response to Alpha Interferon, Gamma Interferon, Poly(I)-poly(C), Tumor Necrosis Factor Alpha, and Ribavirin in Hepatitis C Virus Subgenomic Replicons," *J. Virol.* 77:1092-1104, American Society for Microbiology, United States (2003).

Lanford, R., et al., "Lack of response to exogenous interferon-alpha in the liver of chimpanzees chronically infected with hepatitis C virus," *Hepatology* 46:999-1008, Wiley, United States (2007).

Lima, W., et al, "Combinatorial Screening and Rational Optimization for Hybridization to Folded Hepatitis C Virus RNA of Oligonucleotides with Biological Antisense Activity," *J. Biol. Chem.* 272:626-638, A237 (1997).

Lisziewicz, J., et al., "Long-term treatment of human immunodeficiency virus-infected cells with antisense oligonucleotide phosphorothioates," *Proc. Natl. Acad. Sci.* 90:3860-3864, National Academy of Sciences, United States (1993).

Manoharan, M., et al., "Novel Functionalization of the Sugar Moiety of Nucleic Acids for Multiple Labeling in the Minor Groove," *Tetrahedron Letters* 34:7171-7174, Pergamon Press, PLC., United Kingdom (1991).

Martinez, J., et al., Single-Stranded Antisense siRNAs Guide Target RNA Cleavage in RNAi, *Cell* 110:563-574, Cell Press, United States (2002).

Matz, M., et al., "Early post-transplant urinary IP-10 expression after kidney transplantation is predictive of short- and long-term graft function," *Kidney Int.* 69:1683-1690, Nature Publishing Group (2006).

McManus, M., and Sharp, P., "Gene Silencing in Mammals by Small Interfering RNAs," *Nat. Rev. Genet.* 3:737-747, Nature Publishing Group, United Kingdom (2002).

Möröy, T., et al., "Structure and expression of hcr, a locus rearranged with c-myc in a woodchuck hepatocellular carcinoma," *Oncogene* 4:59-65, Nature Publishing Group, United Kingdom (1989).

Neuman, B., et al., "Antisense Morpholino-Oligomers Directed against the 5' End of the Genome Inhibit Coronavirus Proliferation and Growth," *J. Virol.* 78:5891-5899, American Society for Microbiology, United States (2004).

Nulf, C. And Corey, D., "Intracellular inhibition of hepatitis C virus (HCV) internal ribosomal entry site (IRES)-dependent translation by peptide nucleic acids (PNAs) and locked nucleic acids (LNAs)," *Nucleic Acids Res.* 32:3792-3798, Oxford University Press, United Kingdom (2004).

Ørom, U., et al., "LNA-modified oligonucleotides mediate specific inhibition of microRNA function," *Gene* 372:137-141, Elsevier, Inc., The Netherlands (2006).

Paushkin, S., et al., "The SMN complex, an assemblyosome of ribonucleoproteins," *Curr. Opin. Cell Biol.* 14:305-312, Elsevier Science Ltd., United Kingdom (2002).

Pedersen, D., et al., "Preparation of LNA Phosphoramidites," *Synthesis* 6:802-808, Thieme/Academic Press, Germany (2002) 1.

Pedersen, D., and Koch, T., "Analogues of LNA (Locked Nucleic Acid). Synthesis of the 2'Thio-LNA Thymine and 5-Methyl Cytosine Phosphoramidites," *Synthesis* 4:578-582, Thieme/Academic Press, Germany (2003).

Petri, A., et al., "MicroRNA Silencing in Primates: Towards Development of Novel Therapeutics," *Can. Res.* 69:393-395, American Association for Cancer Research, United States (2009).

Prakash, T., et al., "Antisense Oligonucleotides Containing Conformationally Constrained 2',4'-(N-Methoxy)aminomethylene and 2',4'-Aminooxymethylene and 2'-O,4'-C-Aminomethylene Bridged Nucleoside Analogues Show Improved Potency in Animal Models," *J. Med. Chem.* 53:1636-1650, American Chemical Society, United States (2010).

Randall, G., et al, "Cellular cofactors affecting hepatitis C virus infection and replication," *Proc. Natl. Acad. Sci. USA* 104:12884-12889, National Academy of Sciences, United States (2007).

Rosenbohm, C., et al., "Synthesis of 2'-amino-LNA: a new strategy," *Org. Biomol. Chem.* 1:655-663, Royal Society of Chemistry, United Kingdom (2003).

Saeed, A., et al., "TM4: A Free, Open-Source System for Microarray Data Management and Analysis," *Bio Techniques* 34:374-378, Informa Healthcare USA, Inc., United Kingdom (2003).

Samuel, D., "Hepatitis C, Interferon, and Risk of Rejection After Liver Transplantation," *Liver Transpl.* 10:868-887, Wiley InterScience, United States (2004).

Santaris Pharma, Nature Genetics Ad, Jun. 2006 [powerpoint slide], 1 page.

Sazani, P., et al., "Nuclear antisense effects of neutral, anionic and cationic oligonucleotide analogs," *Nucleic Acids. Res.* 29:3965-3974, Oxford University Press, United Kingdom (2001).

Schwarz, D., et al., "Evidence that siRNAs Function as Guides, Not Primers, in the Drosophila and Human RNAi Pathways," *Mol. Cell* 10:537-548, Cell Press, United States (2002).

Seth, P., et al., "Synthesis and Biophysical Evaluation of 2',4'-Constrained 2'O-Methoxyethyl and 2',4'-Constrained 2'O-Ethyl Nucleic Acid Analogues," *J. Org. Chem.* 75:1569-1581, American Chemical Society, United States (2010).

Singh, S. And Wengel, J., "Synthesis of Novel Bicyclo[2.2.1] Ribonucleosides: 2'-Amino- and 2'-Thio-LNA Monomeric Nucleosides," *J. Org. Chem.* 63:6078-6079, American Chemical Society, United States (1998).

Sørensen, M., et al,"α-L-ribo-Configured Locked Nucleic Acid (α-L-LNA): Synthesis and Properties," *J. Am. Chem. Soc.* 124:2164-2176, American Chemical Society, United States (2002).

Tallet-Lopez, B., et al., "Antisense oligonucleotides targeted to the domain IIId of the hepatitis C virus IRES compete with 40S ribosomal subunit binding and prevent in vitro translation," *Nucleic Acids Res.* 31:734-742, Oxford University Press, United Kingdom (2003).

Tam, W., "Identification and characterization of human BIC, a gene on chromosome 21 that encodes a noncoding RNA," *Gene* 274:157-167, Elsevier, The Netherlands (2001).

Tijsterman, M., et al., "RNA Helicase MUT-14-Depedent Gene Silencing Triggered in C.elegans by Short Antisense RNAs," *Science* 295:694-697, American Assn. for the Advancement of Science, United States (2002).

Uhlmann, E., "Recent advances in the medicinal chemistry of antisense oligonucleotides," *Curr. Opin. Drug Discov. Develop.* 3:203-213, Pharma Press Ltd., United Kingdom (2000).

Wagner, R., "Gene inhibition using antisense oligodeoxynucleotides," *Nature* 372:333-335, Nature Publishing Group, United Kingdom (1994).

Wagner, R., et al., "Potent and selective inhibition of gene expression by an antisense heptanucleotide," *Nat. Biotechnol.* 14:840-844, Nature Publishing Group, United States (1996).

Wahlestedt, C., et al., "Potent and nontoxic antisense oligonucleotides containing locked nucleic acids," *Proc. Natl. Acad. Sci. USA* 97:5633-5638, National Academy of the Sciences, United States (2000).

Walter, T., et al., "Rejection Under Alpha Interferon Therapy in Liver Transplant Recipients," *American Journal of Transplantation* 7:177-184, Blackwell Munksgaard, Denmark (2007).

Yu, J., et al., "RNA interference by expression of short-interfering RNAs and hairpin RNAs in mammalian cells," *Proc. Natl. Acad. Sci.* 99:6047-6052, National Academy of Sciences, United States (2002).

Zhang, H., et al., "Antisense Oligonucleotide Inhibition of Hepatisis C Virus (HCV) Gene Expression in Livers of Mice Infected with an HCV-Vaccinia Virus Recombinant," *Antimicrobial Agents and Chemotherapy* 43:347-353, American Society for Microbiology, United States (1999).

Zhao, Y., et al., "Serum response factor regulates a muscle-specific microRNA that targets Hand2 during cardiogenesis," *Nature* 436:214-220, Nature Publishing Group, United Kingdom (2005).

International Search Report for International Application No. PCT/EP2008/053309, European Patent Office, mailed on Jul. 18, 2008.

* cited by examiner

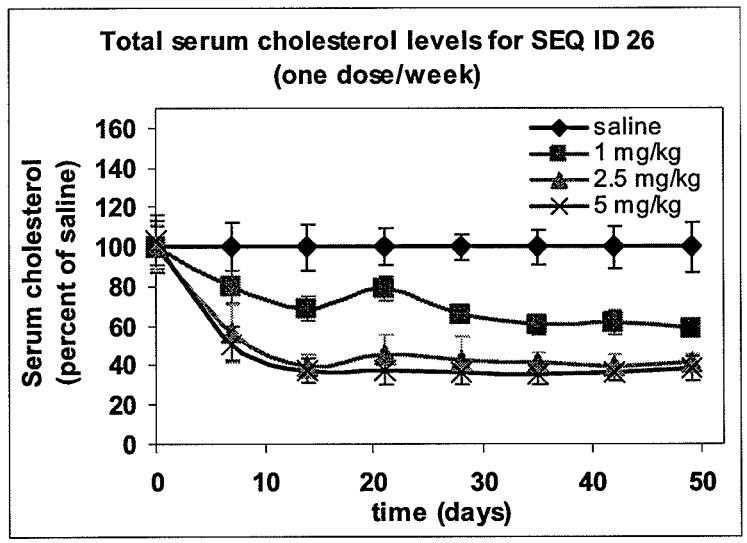
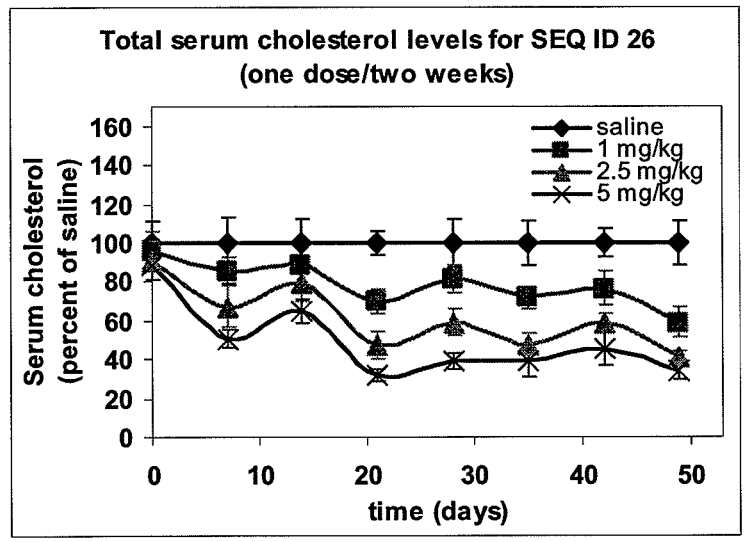
Figure 9 A & B.

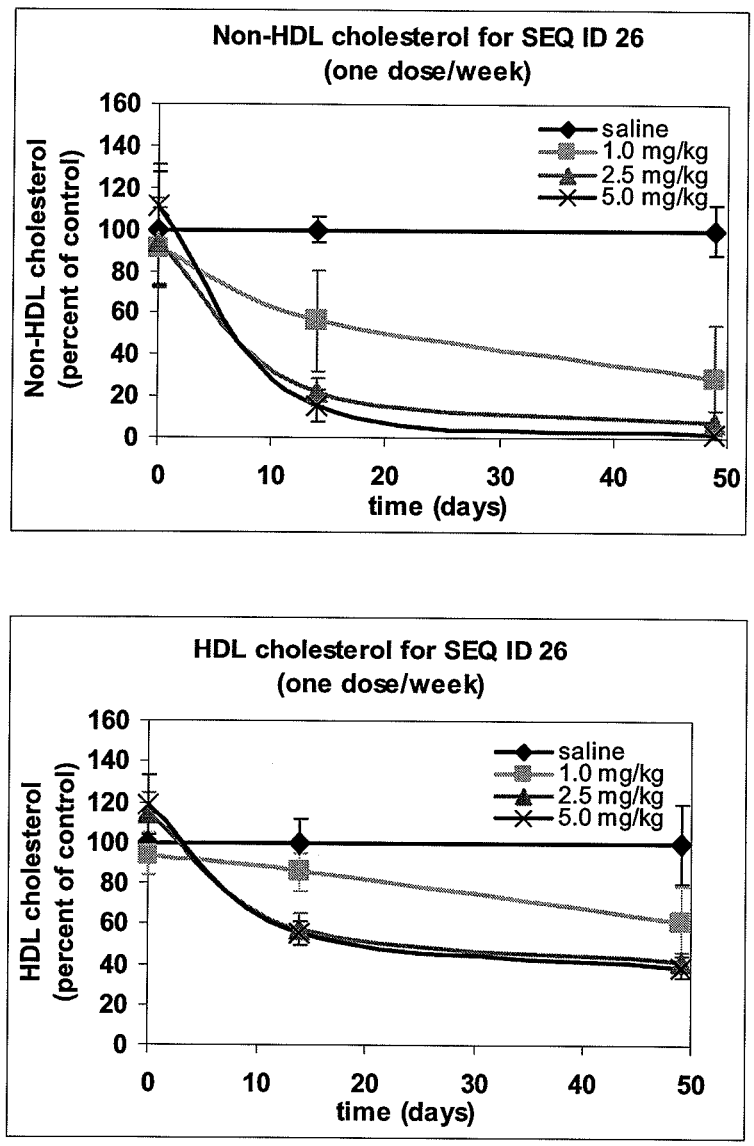
Figure 10 A & B.

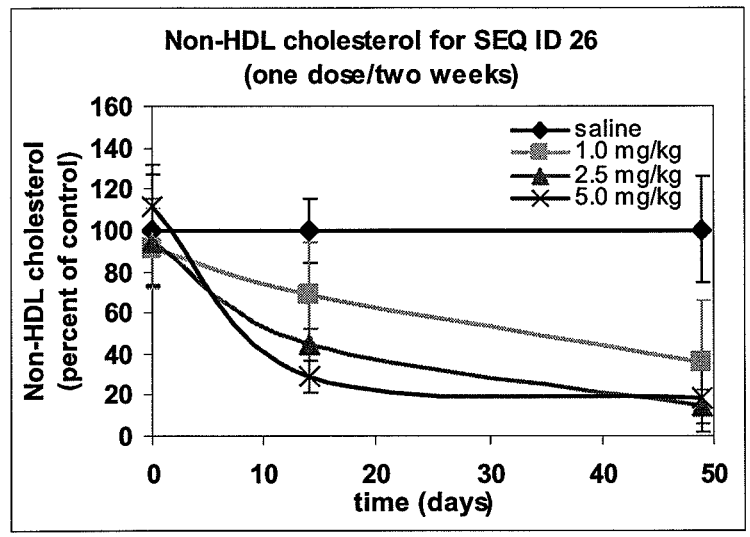
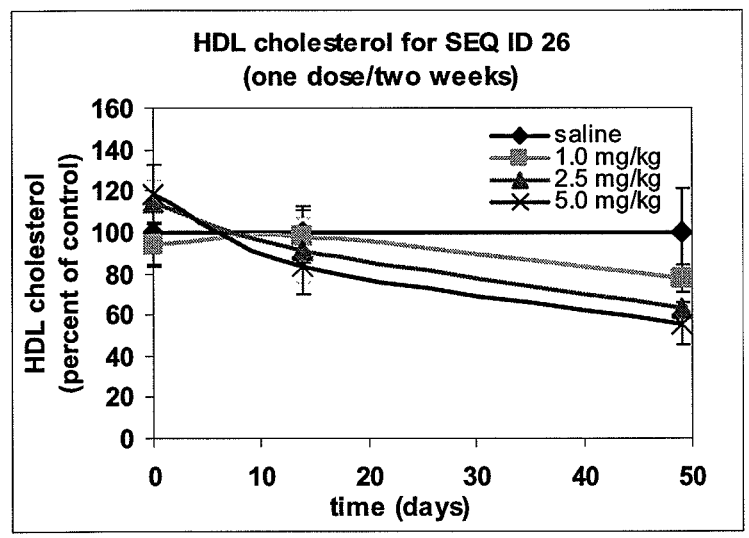
Figure 11 A & B.

RNA ANTAGONIST COMPOUNDS FOR THE INHIBITION OF APO-B100 EXPRESSION

CROSS-REFERENCE TO RELATED APPLICATIONS

The present application is a U.S. National Phase of International Application No. PCT/EP2008/053309, filed Mar. 19, 2008, which claims the benefit of U.S. Provisional Application No. 60/896,419, filed Mar. 22, 2007, and U.S. Provisional Application No. 60/977,409, filed Oct. 4, 2007, each of which is incorporated herein by reference.

REFERENCE TO SEQUENCE LISTING SUBMITTED ELECTRONICALLY

The content of the electronically submitted sequence listing (Name: Sequence_Listing_2.txt; Size: 21,799 bytes; and Date of Creation: May 10, 2010) filed with the application is incorporated herein by reference in its entirety.

FIELD OF THE INVENTION

The invention refers to oligonucleotides directed against the Apo-B100 gene are provided for modulating the expression of Apo-B100. Methods of using these compounds for modulation of Apo-B100 expression and for the treatment of diseases associated with Apo-B100 expression are provided. The oligonucleotides comprise deoxyribonucleosides and locked nucleic acids.

BACKGROUND OF THE INVENTION

See the background section of WO2007/031081 which is hereby incorporated by reference.

To date, strategies aimed at inhibiting apolipoprotein B function have been limited to Lp(a) apheresis, antibodies, antibody fragments and ribozymes. Moreover, low biostability and/or low binding affinity antisense oligonucleotides have been disclosed and claimed in PCT publication WO 00/97662, WO 03/11887 and WO 2004/44181.

Consequently, there remains a need for additional agents capable of effectively antagonize apolipoprotein B function and consequently lower the plasma Lp(a) level.

The present invention provides effective Locked Nucleic Acid (LNA) oligomeric compounds and their use in methods for modulating apolipoprotein B expression, ApB-100, including inhibition of the alternative isoform of apolipoprotein B ApoB-48.

SUMMARY OF THE INVENTION

The invention provides for an oligomeric compound (oligomer) consisting of a total of 10-15 nucleobases, wherein the nucleobase sequence of said compound is present in SEQ ID NO 1, wherein said compound comprises at least 2 or at least 3 nucleotide analogues.

The invention provides for an oligomeric compound consisting of a total of 10-15 nucleobases, wherein the nucleobase sequence of said compound corresponds to a contiguous sub-sequence present in SEQ ID NO 1, wherein said compound comprises at least 2 or at least 3 nucleotide analogues.

The invention provides for a conjugate comprising the compound according to the invention and at least one non-nucleotide or non-polynucleotide moiety covalently attached to said compound.

The invention provides for a pharmaceutical composition comprising a compound or a conjugate according to the invention, and a pharmaceutically acceptable diluent, carrier or adjuvant.

The invention provides for a compound or a conjugate as according to the invention for use as a medicament.

The invention provides for the use of a compound or a conjugate according to the invention for the manufacture of a medicament for the treatment of abnormal levels of Apo-B100 or a disease or condition correlated thereto.

The invention provides for a medicament comprising the compound according to the invention or the conjugate according to the invention, for the treatment of abnormal levels of Apo-B100 or a disease or condition correlated thereto, such as atherosclerosis, hypercholesterolemia or hyperlipidemia.

The invention provides for a method of treating a subject suffering from a disease or condition selected from atherosclerosis, hypercholesterolemia and hyperlipidemia, the method comprising the step of administering a pharmaceutical composition or conjugate or medicament according to the invention to the subject in need thereof.

The invention provides for a method for down-regulation apolipoprotein B, the method comprising the step of administering a pharmaceutical composition or conjugate or medicament according to the invention to a subject, such as a subject suffering from a medical condition selected from the group consisting of: atherosclerosis, hypercholesterolemia or hyperlipidemia.

The invention provides for a method for down-regulation apolipoprotein B (ApoB) mRNA in a cell which is expressing said ApoB mRNA, said method comprising the step of administering the compound of the invention to said cell so as to down-regulate said ApoB mRNA.

The invention provides for a method for down-regulation apolipoprotein B (ApoB) protein in a cell which is expressing said ApoB protein, said method comprising the step of administering the compound of the invention to said cell so as to down-regulate said ApoB protein.

BRIEF DESCRIPTION OF THE FIGURES

FIG. 9: Serum total cholesterol presented in percentage of the control group (saline) after dosing 1, 2.5 or 5 mg/kg/dose SEQ ID NO 26 A: once a week (days 0, 7, 14, 21, 28, 35, 42) or B: once every second week (days 0, 14, 28 and 42). All animals are sacrificed 49 days after the 1. dosing. Data is presented as mean±SD, n=7.

FIG. 10: Total cholesterol in A) non-HDL and B) HDL fractions separated from plasma by ultracentrifugation. C57BL/6J mice were dosed SEQ ID NO 26 once a week at 1, 2.5 or 5 mg/kg, plasma was sampled one week after dosing, just before the next dosing. Data represents mean±SD and is presented relative to the saline control group, n=5.

FIG. 11: Total cholesterol in A) non-HDL and B) HDL fractions separated from plasma by ultracentrifugation. C57BL/6J mice were dosed SEQ ID NO 26 once every two weeks at 1, 2.5 or 5 mg/kg, plasma was sampled one week or two weeks after dosing. Data represents mean±SD and is presented relative to the saline control group, n=5.

DETAILED DESCRIPTION OF THE INVENTION

Figure 1:
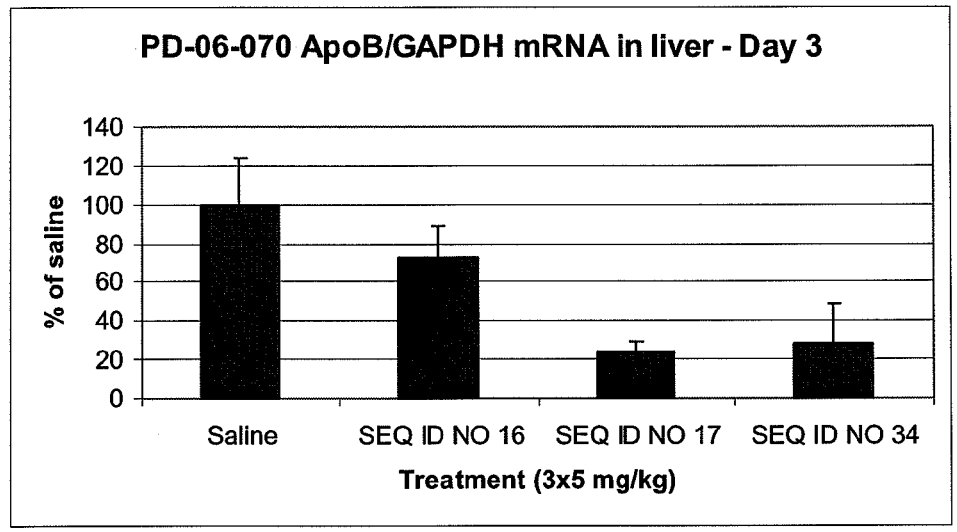
FIG. 1. The apoB-100 mRNA expression was measured by qPCR normalized to the house keeping gene GAPDH and presented relative to the saline group. Mice (n=3 or 5) were dosed 3 consecutive days and sacrifice 24 hours after the last dosing, liver was isolated and analysed.

U.S. provisional applications 60/896,419 and 60/977,409 are hereby incorporated by reference.

Oligomeric Compounds

The present invention employs oligomeric compounds, particularly antisense oligonucleotides, for use in inhibition of the function of nucleic acid molecules encoding apolipoprotein B (such as Apo-B100 and/or ApoB-48) which leads to a decrease in the number of functional proteins produced.

The present invention provides compositions and methods for modulating the expression of apolipoprotein B (Apo-B100/Apo-B48). In particular, this invention relates to oligonucleotide compounds over specific motifs targeting apolipoprotein B. These motifs are SEQ ID NOS: 2-15, in particular SEQ ID NOS: 5, 9 and 13. Specific designs of LNA containing oligonucleotide compounds are also disclosed. Specifically preferred compounds are SEQ ID NOS:17-40, and/or 41-49, in particular SEQ ID NOS: 16, 17, 26 and 34. The compounds of the invention are potent inhibitors of apoliprotein mRNA and protein expression.

As used herein, the term "target nucleic acid" encompasses DNA encoding the Apo-B100, RNA (including pre-mRNA and mRNA and mRNA edit) transcribed from such DNA, and also cDNA derived from such RNA.

The "target protein" is mammalian apolipoprotein B, preferably human apolipoprotein B. It will be recognised that as ApoB-100 and ApoB-48 both originate from the same genetic sequence, that the oligomeric compounds according to the invention may be used for down-regulation of either, or both forms of apolipoprotein B, and both ApoB-100 encoding mRNA, and the RNA edited form, which encodes Apo-B48.

As used herein, the term "gene" means the gene including exons, introns, non-coding 5' and 3' regions and regulatory elements and all currently known variants thereof and any further variants, which may be elucidated.

As used herein, the term "mRNA" means the presently known mRNA transcript(s) of a targeted gene, and any further transcripts, which may be identified.

As used herein, the term "modulation" means either an increase (stimulation) or a decrease (inhibition) in the expression of a gene. In the present invention, inhibition is the preferred form of modulation of gene expression and mRNA is a preferred target.

As used herein, the term "targeting" an antisense compound to a particular target nucleic acid means providing the antisense oligonucleotide to the cell, animal or human in such a way that the antisense compound are able to bind to and modulate the function of its intended target.

The terms "Oligomeric compound", which is interchangeable with the term "oligomer", "oligonucleotide", "oligo", and "oligonucleotide compound", refer, in the context of the present invention, to an oligomer, i.e. a nucleic acid polymer (e.g. ribonucleic acid (RNA) or deoxyribonucleic acid (DNA)) or nucleic acid analogue of those known in the art, preferably Locked Nucleic Acid (LNA), or a mixture thereof). This term includes oligonucleotides composed of naturally occurring nucleobases, sugars and internucleoside (backbone) linkages as well as oligonucleotides having non-naturally-occurring portions which function similarly or with specific improved functions. Fully or partly modified or substituted oligonucleotides are often preferred over native forms because of several desirable properties of such oligonucleotides, such as for instance, the ability to penetrate a cell membrane, good resistance to extra- and intracellular nucleases, high affinity and specificity for the nucleic acid target. The LNA analogue is particularly preferred, for example, regarding the above-mentioned properties. Therefore, in a highly preferable embodiment, the terms "oligomeric compound", "oligonucleotide", "oligo", "oligomer", and "oligonucleotide compound" according to the invention, are compounds which are built up of both nucleotide and nucleotide analogue units, such as LNA units to form a polymeric compound (oligomer) of between 10-15 (contiguous) nucleotides/nucleotide analogues.

The oligomeric compounds are preferably antisense oligomeric compounds, also referred to as 'antisense oligonucleotides' and 'antisense inhibitors'.

The antisense inhibitors are single stranded oligonucleotides. The single stranded oligonucleotides are preferably complementary to the corresponding region of the target nucleic acid.

Typically, single stranded 'antisense' oligonucleotides specifically interact with the mRNA of the target gene, causing either targeted degredation of the mRNA, for example via the RNaseH mechanism, or otherwise preventing translation.

By the term "unit" is understood a monomer.

The oligomeric compounds of the invention are capable of hybridizing to either the apolipoprotein B messenger RNA(s) and/or the sense or complementary mammalian apolipoprotein B (Apo-B) DNA strands. NCBI Accession No. NM_000384 provides an mRNA sequence for human apolipoprotein B. It is highly preferably that the oligomeric compound of the invention is capable of hybridising to the human apolipoprotein encoded by the nucleic acid disclosed in NCBI Accession No. NM_000384, or reverse complement thereof, including, in a preferred embodiment, mRNA nucleic acid targets derived from said human apolipoprotein.

The term "at least [an integer]" comprises the integers larger than or equal to said integer, such as 1, 2, 3, 4, 5, 6, 7, 8, 9, 10, 11, 12, 13, 14, 15, 16, 17, 18, 19, 20, 21 and so forth.

In an interesting embodiment, the 3' end of the compound of the invention comprises a nucleotide, rather than a nucleotide analogue.

In a preferred embodiment, the oligonucleotides are capable of hybridising against the target nucleic acid, such as an ApoB mRNA, to form a duplex with a $T_m$ of at least 30° C., such as at least 37° C., such as at least 40° C., at least 50° C., at least 55° C., or at least 60° C. In one aspect the $T_m$ is between 37° C. and 80° C., such as between 50 and 70° C. In one aspect the $T_m$ is between 30° C. and 40° C.

Measurement of $T_m$

A 3 µM solution of the compound in 10 mM sodium phosphate/100 mM NaCl/0.1 nM EDTA, pH 7.0 is mixed with its complement DNA or RNA oligonucleotide at 3 µM concentration in 10 mM sodium phosphate/100 mM NaCl/0.1 nM EDTA, pH 7.0 at 90° C. for a minute and allowed to cool down to room temperature. The melting curve of the duplex is then determined by measuring the absorbance at 260 nm with a heating rate of 1° C./min. in the range of 25 to 95° C. The $T_m$ is measured as the maximum of the first derivative of the melting curve.

In one embodiment the oligomeric compound according to the invention may target the DNA encoding mammalian ApoB.

The term "nucleobase" as used herein refers to both naturally occurring nucleotides, such as DNA and RNA nucleotides (units), and non-naturally occurring nucleotides, referred to as nucleotide analogue (units).

Sequences

The invention is directed to an oligomeric compound, consisting of 10-15, such as 11-15, 12-15, 13-15, in particular 12-14 nucleobases wherein the nucleobase sequence is present in SEQ ID NO. 1. The list of such sequences is given in Table 1. In one embodiment, the preferred groups of sequences present in SEQ ID NO 1 are SEQ ID NO: 4-15.

The sequence motifs in the target to which these preferred oligomeric compounds are complementary (referred to as "hot spots") are preferred sites for targeting. It should be noted that the motifs referred to in the sequence listing are referred to as DNA sequences—however these may refer to other nucleotides or nucleotide analogues which, in the contiguous sequence of the compound retain the same sequence, or subsequence of bases.

The invention provides for an oligomeric compound consisting of a total of 10-15 nucleobases, wherein the nucleobase sequence of said compound is present in SEQ ID NO 1, wherein said compound comprises at least 2 or at least 3 nucleotide analogues.

Suitably, the oligomeric compound of the invention consists of a contiguous nucleobase sequence of a total of 10-15 nucleobases in length.

In one embodiment the nucleobase sequence selected from the group consisting of SEQ ID NOS 2, 3, 4, 5, 6, 7, 8, 9, 10, 11, 12, 13, 14, 15 (motif sequences), or a corresponding subsequence thereof.

A 'corresponding subsequence' refers to the situation where the oligomer of the invention is shorter than the respective sequence selected from the group consisting of SEQ ID NOS 1, 2, 3, 4, 5, 6, 7, 8, 9, 10, 11, 12, 13, 14, 15, but the contiguous sequence of bases present in the oligomer is found within the respective sequence.

The terms "corresponding to" and "corresponds to" refer to the comparison between the nucleobase sequence of the oligomer (the contiguous nucleobase sequence) and the equivalent nucleotide sequence of i) the reverse complement of the nucleic acid target, such as the mRNA which encodes the ApoB target protein, and/or ii) the sequence of nucleotides provided herein such as the group consisting of SEQ ID NOS: 1-15. Nucleotide analogues are compared directly to their equivalent or corresponding nucleotides. Therefore, in one embodiment, the terms "corresponding to"/"corresponds to" refer to the comparison between the combined sequence of nucleotides and nucleotide analogues of the oligomeric compound of the invention, or subsequence thereof, and the equivalent nucleotide sequence of Apolipoprotein B nucleic acid sequence (i.e. the nucleic acid target).

The terms "corresponding nucleoside/nucleotide analogue" and "corresponding nucleoside/nucleotide" are intended to indicate that the nitrogenous base in the nucleoside/nucleotide analogue and the nucleoside/nucleotide is identical. For example, when the 2-deoxyribose unit of the nucleotide is linked to an adenine, the "corresponding nucleoside analogue" contains a pentose unit (different from 2-deoxyribose) linked to an adenine.

The term "nucleic acid" is defined as a molecule formed by covalent linkage of two or more nucleotides. The terms "nucleic acid" and "polynucleotide" are used interchangeable herein. For example, DNA and RNA are nucleic acids.

In one embodiment the compound of the invention is selected from the group consisting of SEQ ID NO: 17, 18, 19, 20, 21, 22, 23, 24 and 25.

In one embodiment the compound of the invention is selected from the group consisting of SEQ ID NO: 26, 27, 28, 29, 30, 31, 32, and 33.

In one embodiment the compound of the invention is selected from the group consisting of SEQ ID NO 34, 35, 36, 37, 38, 39 and 40.

In one embodiment the compound of the invention is selected from the group consisting of SEQ ID NO 16, 17, 26 and 34; or 17, 26 and 34.

In one embodiment the compound of the invention is selected from the group consisting of SEQ ID NO 41-49.

Gapmers

In a preferred embodiment, the nucleobase sequence of the compound of the invention comprises or consists, in a 5' to 3' direction i) region A: a stretch of 2-4 nucleotide analogues, followed by ii) region B: a stretch of 6-11 nucleotides (such as DNA nucleotides), which is followed by iii) region C: a stretch of 2-4 nucleotide analogues, and optionally iv) one or two nucleotides (D).

In one embodiment region A has a length of 1 nucleotide analogues. In one embodiment region A has a length of 2 nucleotide analogues. In one embodiment region A has a length of 3 nucleotide analogues. In one embodiment region A has a length of 4 nucleotide analogues. In one embodiment region C has a length of 1 nucleotide analogues. In one embodiment region C has a length of 2 nucleotide analogues. In one embodiment region C has a length of 3 nucleotide analogues. In one embodiment region C has a length of 4 nucleotide analogues. In one embodiment region B has a length of between 7 and 10 nucleotides (such as DNA nucleotides), such as 8 or 9 nucleotides (such as DNA nucleotides). In one embodiment the compound according to the invention has a length of from 12-15 nucleobases. In one embodiment the compound according to the invention has a length of 12, 13, or 14 nucleobases. In one embodiment, the gapmer may be of formula in a 5' to 3' direction D-A-B-C.

Internucleoside Linkages

In one embodiment the nucleobase sequence of the compound of the invention comprises a internucleobase linkage group selected from the group consisting of a phosphate group, a phosphodiester group, a phosphorothioate group and a boranophosphate group, the internucleoside linkage may be —O—P(O)$_2$—O—, —O—P(O,S)—O—. In one embodiment, the internucleoside linkages are in phosphate group and/or a phosphorothioate group. In a particular embodiment, all nucleotides comprise a phosphorothioate group. In one embodiment, some or all of the nucleotides are linked to each other by means of a phosphorothioate group. Suitably, all nucleotides are linked to each other by means of a phosphorothioate group.

In one embodiment, the internucleobase linkage groups between the nucleobase units of the nucleobase sequence of the compound of the invention are independently selected from either phosphorothioate or phosphodiester linkage groups.

In one embodiment region A comprises at least one phosphodiester linkage between two nucleotide analogue units, or a nucleotide analogue unit and a nucleotide unit. It will be understood that the linkage group between a nucleotide analogue and a nucleotide unit in this context refers to the linkage group between regions A and B.

In one embodiment region C comprises at least one phosphodiester linkage between two nucleotide analogue units, or a nucleotide analogue unit and a nucleotide unit. It will be understood that the linkage group between a nucleotide analogue and a nucleotide unit in this context refers to the linkage group between regions B and C.

In one embodiment the internucleotide linkages between the nucleotides of region B are phosphorothioate. In one embodiment the internucleobase linkage between the 3' nucleotide analogue of A and the 5' nucleotide of region B is a phosphorothioate.

In one embodiment the internucleobase linkage between the 3' nucleotide of region B and the 5' nucleotide analogue of region C is a phosphorothioate. In one embodiment the internucleobase linkage between the 3' nucleotide analogue of A and the 5' nucleotide of region B is a phosphodiester. In one embodiment the internucleobase linkage between the 3' nucleotide of region B and the 5' nucleotide analogue of region C is a phosphodiester. In one embodiment the internucleobase linkage between the two 5' nucleotide analogues of region A are phosphodiester. In one embodiment the internucleobase linkage between the two 3' nucleotide analogues of region C are phosphodiester. In one embodiment the internucleobase linkage between the two 3' nucleotide analogues of region A are phosphodiester. In one embodiment the internucleobase linkage between the two 5' nucleotide analogues of region C are phosphodiester. In one embodiment region A has a length of 4 nucleotide analogues and internucleobase linkage between the two middle nucleotide analogues of region A are phosphodiester. In one embodiment region C has a length of 4 nucleotide analogues and internucleobase linkage between the two middle nucleotide analogues of region C are phosphodiester. In one embodiment all the internucleobase linkages between nucleotide analogues present in the compound of the invention are phosphodiester.

In one embodiment, such as the embodiments referred to above, as suitable and where not specifically indicated all remaining internucleobase linkages are either phosphodiester or phosphorothioate, or in one separate embodiment a mixture thereof. In one embodiment all the internucleobase linkage groups are phosphorothioate.

Nucleotide Analogues

When used herein, the term "nucleotide analogue" refers to a non-natural occurring nucleotide wherein, for example in one preferred embodiment, either the ribose unit is different from 2-deoxyribose and/or the nitrogenous base is different from A, C, T and G and/or the internucleoside phosphate linkage group is different. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1:

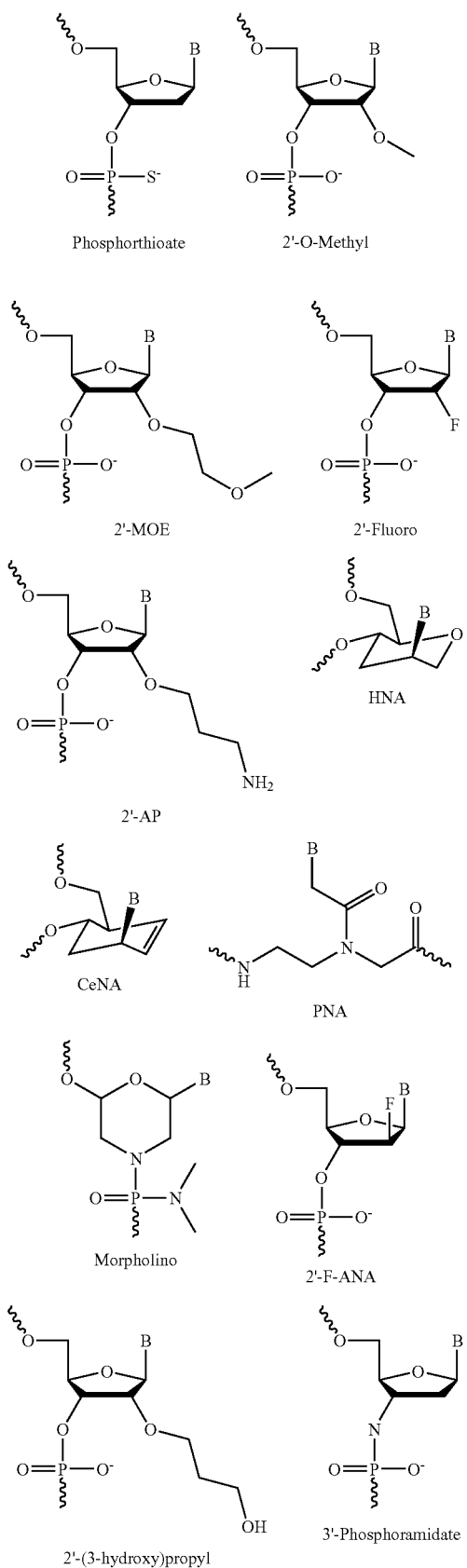

Scheme 1

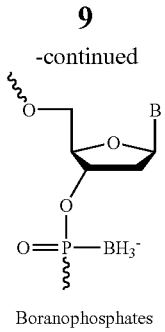

Boranophosphates

Suitable nucleotide analogues for use in the oligonucleotide of the invention are independently selected from the group consisting of: 2'-O-alkyl-RNA monomers, 2'-amino-DNA monomers, 2'-fluoro-DNA monomers, LNA monomers, arabino nucleic acid (ANA) monomers, 2'-fluoro-ANA monomers, HNA monomers, INA monomers.

2'-O-methoxyethyl-RNA, 2'-fluoro-DNA monomers and LNA are preferred and as such the oligonucleotide of the invention may comprise nucleotide analogues which are independently selected from these three types of analogue, or may comprise of only one type selected from the three types. In a most preferred embodiment the oligonucleotide comprises only LNA nucleotide analogues and nucleotides (RNA or DNA, most preferably DNA nucleotides).

In one embodiment the nucleotide analogues present within the compound of the invention, such as in regions A and C are independently selected from the group consisting of: 2'-O-alkyl-RNA monomers, 2'-amino-DNA monomers, 2'-fluoro-DNA monomers, LNA monomers, arabino nucleic acid (ANA) monomers, 2'-fluoro-ANA monomers, HNA monomers, INA monomers.

In one embodiment the nucleotide analogues are independently selected from the group consisting of 2'-MOE-RNA (2'-O-methoxyethyl-RNA), 2'Fluoro-DNA, and LNA.

In one embodiment at least one of said nucleotide analogues is a locked nucleic acid (LNA).

In one embodiment at least one of said nucleotide analogues is 2'-MOE-RNA, such as 2, 3, 4, 5, 6, 7 or 8 2'-MOE-RNA nucleobase units.

In one embodiment at least one of said nucleotide analogues is 2'-fluoro DNA, such as 2, 3, 4, 5, 6, 7 or 8 2'-fluoro-DNA nucleobase units.

In one embodiment 2, 3, 4, 5, 6, 7 or 8 of the nucleotide analogues are LNA and any remaining nucleotide analogue may be selected from the groups of nucleotide analogues referred to herein.

The oligomeric compound according to the invention preferably comprises at least two or at least three nucleotide analogues. The at least two or at least three three nucleotide analogues are preferably locked nucleic acid nucleotide analogues (LNA), and the oligomeric compound which comprises such nucleotide analogues are referred to herein as "LNA oligomeric compound", "LNA oligonucleotide compound" and "LNA oligonucleotide".

In one embodiment all the nucleotide analogues are LNA.

In one embodiment the nucleotide analogues are not PNA.

In one embodiment the LNA nucleotide analogues present within the compound of the invention is/are selected from beta-D-oxy-LNA, alpha-L-oxy-LNA, beta-D-amino-LNA and beta-D-thio-LNA.

Preferably, the oligomeric compound, such as an antisense oligonucleotide, may comprise both LNA and DNA units. Preferably the combined total of LNA and DNA units is between 10-15, including 11, 12, 13, and 14.

In one embodiment, within the oligomeric compound according to the invention, such as an antisense oligonucleotide, which comprises LNA, all LNA C residues are 5' methyl-Cytosine.

Locked Nucleic Acid (LNA)

The term "LNA" refers to a bicyclic nucleotide analogue, known as "Locked Nucleic Acid". It may refer to an LNA monomer, or, when used in the context of an "LNA oligonucleotide" refers to an oligonucleotide containing one or more such bicyclic nucleotide analogues. The LNA used in the oligonucleotide compounds of the invention preferably has the structure of the general formula I

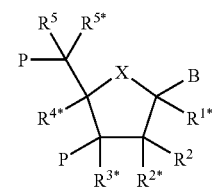

wherein X is selected from —O—, —S—, —N($R^{N*}$)—, —C($R^6R^{6*}$)—;

B is selected from hydrogen, optionally substituted $C_{1-4}$-alkoxy, optionally substituted $C_{1-4}$-alkyl, optionally substituted $C_{1-4}$-acyloxy, natural or non-natural nucleobases, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{4*}$ and $R^{2*}$ together designate a biradical consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, >C=Z, wherein Z is selected from O, S, and N($R^a$), and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, cycloalkyl, cycloalkyloxy-carbonyl, cycloalkyloxy, cycloalkylcarbonyl, heterocycloalkyl, heterocycloalkyloxy-carbonyl, heterocycloalkyloxy, heterocycloalkylcarbonyl, amino, mono- and di($C_{1-6}$-alkyl)amino, tris($C_{1-6}$-alkyl)ammonium, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$) or together may form a spiro biradical consisting of a 1-5 carbon atom(s) alkylene chain which is optionally interrupted and/or terminated by one or more heteroatoms/groups selected from —O—, —S—, and —(NR$^N$)—where R$^N$ is selected from hydrogen and C$_{1-4}$-alkyl, and each of the substituents R$^{1*}$, R$^2$, R$^3$, R$^5$, R$^{5*}$, R$^6$ and R$^{6*}$, are independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, cycloalkyl, cycloalkyloxy-carbonyl, cycloalkyloxy, cycloalkylcarbonyl, heterocycloalkyl, heterocycloalkyloxy-carbonyl, heterocycloalkyloxy, heterocycloalkylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkylcarbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present and not involved in a biradical, is selected from hydrogen and C$_{1-4}$-alkyl; and basic salts and acid addition salts thereof;

In one embodiment R$^{5*}$ is selected from H, —CH$_3$, —CH$_2$—CH$_3$, —CH$_2$—O—CH$_3$, and —CH═CH$_2$.

In one embodiment, R$^{4*}$ and R$^{2*}$ together designate a biradical selected from —C(R$^a$R$^b$)—O—, —C(R$^a$R$^b$)—C(R$^c$R$^d$)—O—, —C(R$^a$R$^b$)—C(R$^c$R$^d$)—C(R$^e$R$^f$)—O—, —C(R$^a$R$^b$)—O—C(R$^c$R$^d$)—, —C(R$^a$R$^b$)—O—C(R$^c$R$^d$)—O—, —C(R$^a$R$^b$)—C(R$^c$R$^d$)—, —C(R$^a$R$^b$)—C(R$^c$R$^d$)—C(R$^e$R$^f$)—, —C(R$^a$)═C(R$^b$)—C(R$^c$R$^d$)—, —C(R$^a$R$^b$)—N(R$^c$)—, —C(R$^a$R$^b$)—C(R$^c$R$^d$)—N(R$^e$)—, —C(R$^a$R$^b$)—N(R$^c$)—O—, and —C(R$^a$R$^b$)—S—, —C(R$^a$R$^b$)—C(R$^c$R$^d$)—S—, wherein R$^a$, R$^b$, R$^c$, R$^d$, R$^e$, and R$^f$ each is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, cycloalkyl, cycloalkyloxy-carbonyl, cycloalkyloxy, cycloalkylcarbonyl, heterocycloalkyl, heterocycloalkyloxy-carbonyl, heterocycloalkyloxy, heterocycloalkylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl) amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted and where two geminal substituents together may designate optionally substituted methylene (═CH$_2$) or together may form a spiro biradical consisting of a 1-5 carbon atom(s) alkylene chain which is optionally interrupted and/or terminated by one or more heteroatoms/groups selected from —O—, —S—, and —(NR$^N$)— where R$^N$ is selected from hydrogen and C$_{1-4}$-alkyl.

In a further embodiment R$^{4*}$ and R$^{2*}$ together designate a biradical selected from —CH$_2$—O—, —CH$_2$—S—, —CH$_2$—NH—, —CH$_2$—N(CH$_3$)—, —CH$_2$—CH$_2$—O—, —CH$_2$—CH(CH$_3$)—, —CH$_2$—CH$_2$—S—, —CH$_2$—CH$_2$—NH—, —CH$_2$—CH$_2$—CH$_2$—, —CH$_2$—CH$_2$—CH$_2$—O—, —CH$_2$—CH$_2$—CH(CH$_3$)—, —CH═CH—CH$_2$—, —CH$_2$—O—CH$_2$—O—, —CH$_2$—NH—O—, —CH$_2$—N(CH$_3$)—O—, —CH$_2$—O—CH$_2$—, —CH(CH$_3$)—O—, —CH(CH$_2$—O—CH$_3$)—O—.

All chiral centers may be found in either R or S orientation.

Preferably, the LNA used in the oligomer of the invention comprises at least one LNA unit according to any of the formulas

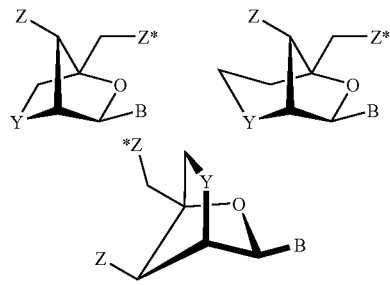

wherein Y is —O—, —S—, —NH—, or N(R$^H$); Z and Z* are independently selected among an internucleoside linkage, a terminal group or a protecting group; B constitutes a natural or non-natural nucleotide base moiety, and R$^H$ is selected from hydrogen and C$_{1-4}$-alkyl.

The term "thio-LNA" comprises a locked nucleotide in which Y in the formulas above represents S. Thio-LNA can be in both beta-D and alpha-L-configuration.

The term "amino-LNA" comprises a locked nucleotide in which Y in the formulas above is selected from —N(H)—, and N(R$^H$)—, where R$^H$ is selected from hydrogen and C$_{1-4}$-alkyl. Amino-LNA can be in both beta-D and alpha-L-configuration.

The term "oxy-LNA" comprises a locked nucleotide in which Y in the formulas above represents —O—. Oxy-LNA can be in both beta-D and alpha-L-configuration.

The term "ENA" comprises a locked nucleotide in which Y in the formulas above is —CH$_2$—O— (where the oxygen atom of —CH$_2$—O— is attached to the 2'-position relative to the base B). ENA can be in both beta-D and alpha-L-configuration.

In a preferred embodiment LNA is selected from beta-D-oxy-LNA, alpha-L-oxy-LNA, beta-D-amino-LNA and beta-D-thio-LNA, in particular beta-D-oxy-LNA.

Specifically preferred LNA units are shown in scheme 2:

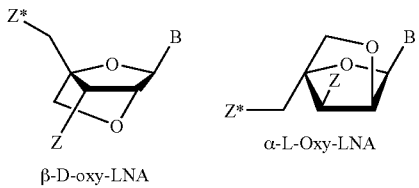

Scheme 2

β-D-oxy-LNA      α-L-Oxy-LNA

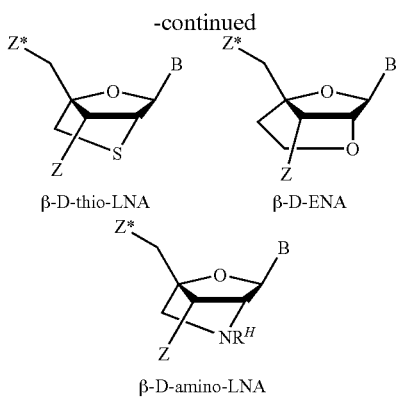

β-D-thio-LNA  β-D-ENA

β-D-amino-LNA

In one embodiment, the Locked Nucleic Acid (LNA) used in the oligonucleotide compounds of the invention has the structure of the general formula:

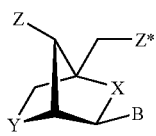

X and Y are independently selected among the groups —O—, —S—, —N(H)—, N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected form hydrogen and C$_{1-4}$-alkyl; Z and Z* are independently selected among an internucleoside linkage, a terminal group or a protecting group; B constitutes a natural or non-natural nucleobase; and the asymmetric groups may be found in either orientation.

The LNA nucleotide analogue building blocks (e.g. β-D-oxy-LNA, β-D-thio-LNA, β-D-amino-LNA and α-L-oxy-LNA) can be prepared following established published procedures—for example see WO2007/031081, hereby incorporated by reference.

Preferably, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$_H$—CO—O—, where R$^H$ is selected form hydrogen and C$_{1-4}$-alkyl.

When used herein, the term "DNA intercalator" means a group which can intercalate into a DNA or RNA helix, duplex or triplex. (Examples of functional parts of DNA intercalators are acridines, anthracene, quinones such as anthraquinone, indole, quinoline, isoquinoline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline)ruthenium-cobalt-enediynes such as calcheamicin, porphyrins, distamycin, netropcin, viologen, daunomycin.)? Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphtoquinone, anthraquinone, naphthoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

In the present context, the term "chelating group" means a molecule that comprises more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context, the term "reporter group" means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalenesulfonyl), DOXYL (N-oxyl-4,4-dimethyloxazolidine), PROXYL (N-oxy-1-2,2,5,5-tetramethylpyrrolidine), TEMPO(N-oxyl-2,2,6,6-tetramethylpiperidine), dinitrophenyl, acridines, coumarins, Cy3 and Cy5 (trademarks for Biological Detection Systems, Inc.), erytrosine, coumaric acid, umbelliferone, Texas Red, rhodamine, tetramethyl rhodamine, Rox, 7-nitrobenzo-2-oxa-1-diazole (NBD), pyrene, fluorescein, europium, ruthenium, samarium, and other rare earth metals), radioisotopic labels, chemiluminescence labels (labels that are detectable via the emission of light during a chemical reaction), spin labels (a free radical (e.g. substituted organic nitroxides) or other paramagnetic probes (e.g. Cu$^{2+}$, Mg$^{2+}$) bound to a biological molecule being detectable by the use of electron spin resonance spectroscopy), enzymes (such as peroxidases, alkaline phosphatases, β-galactosidases, and glucose oxidases), antigens, antibodies, haptens (groups which are able to combine with an antibody, but which cannot initiate an immune response by itself, such as peptides and steroid hormones), carrier systems for cell membrane penetration such as: fatty acid residues, steroid moieties (cholesterol), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, ruthenium, europium, Cy5 and Cy3.

In the present context "ligand" means something which binds. Ligands can comprise functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$-$C_{20}$ alkyl groups optionally interrupted or terminated with one or more heteroatoms such as oxygen atoms, nitrogen atoms, and/or sulphur atoms, optionally comprising aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

Conjugates

The invention also provides for a conjugate comprising the compound of the invention and at least one non-nucleotide or non-polynucleotide moiety covalently attached to said compound. PCT/DK2006/000512 provides suitable ligands and conjugates, which are hereby incorporated by reference.

In one embodiment of the invention, the oligonucleotide may be linked to ligands/conjugates, which may be used, e.g. to increase the cellular uptake of the oligonucleotide. This conjugation can take place at the terminal positions 5'/3'-OH but the ligands may also take place at the sugars and/or the bases. The 3'-OH is preferred site for cholesterol conjugation.

In a preferred embodiment, the oligonucleotide of the invention is conjugated with a moiety which improvise the in vivo uptake, such as cholesterol.

Thus, the oligomeric compound may, e.g., be conjugated or form chimera with non-nucleotide or non-polynucleotide moieties including Peptide Nucleic Acids (PNA), proteins (e.g. antibodies for a target protein), macromolecules, low molecular weight drug substances, fatty acid chains, sugar residues, glycoproteins, polymers (e.g. polyethylene glycol), micelle-forming groups, antibodies, carbohydrates, receptor-binding groups, steroids such as cholesterol, polypeptides, intercalating agents such as an acridine derivative, a long-chain alcohol, a dendrimer, a phospholipid and other lipophilic groups or combinations thereof, etc., just as the Oligomeric compound may be arranged in dimeric or dendritic structures.

In one embodiment referring to the conjugate, the non-nucleotide or non-polynucleotide moiety consists or comprise a sterol group such as cholesterol.

Other such non-nucleotide or non-polynucleotide moieties include, but are not limited to, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

The oligomers of the invention may also be conjugated to active drug substances, for example, aspirin, ibuprofen, a sulfa drug, an antidiabetic, an antibacterial or an antibiotic.

Pharmaceutical Compositions

The invention further provides for a pharmaceutical composition comprising a compound of the invention or a conjugate according to the invention, and a pharmaceutically acceptable diluent, carrier or adjuvant.

Pharmaceutical and other compositions comprising the oligonucleotide compounds of the invention are provided by the present invention.

The pharmaceutical composition may, in one embodiment, further comprise at least one cholesterol-lowering compound.

Suitable cholesterol lowering compounds may be selected from a compound is selected from the group consisting of bile salt sequestering resins (e.g., cholestyramine, colestipol, and colesevelam hydrochloride), HMGCoA-reductase inhibitors (e.g., lovastatin, cerivastatin, prevastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), implitapide, inhibitors of bile acid transporters (apical sodium-dependent bile acid transporters), regulators of hepatic CYP7a, estrogen replacement therapeutics (e.g., tamoxifen), and anti-inflammatories (e.g., glucocorticoids). Combinations with statins may be particularly preferred.

Examples of statins include Atorvastatin™, Cerivastatin™, Fluvastatin™, Lovastatin™, Mevastatin™, Pitavastatin™, Pravastatin™, Rosuvastatin™, and Simvastatin™.

The combined use of the compound of the invention and the statins may allow for a reduction in the dose of the statins, therefore overcoming side effects associated with usual dosage of statins, which include, for example, myalgias, muscle cramps, gastrointestinal symptoms, liver enzyme derangements, myositis, myopathy, rhabdomyolysis (the pathological breakdown of skeletal muscle) which may lead to acute renal failure when muscle breakdown products damage the kidney.

Fibrates, a class of amphipathic carboxylic acids is an alternative class of compound which are often combined with statin use, despite an increased frequency of rhabdomyolysis which has been reported with the combined use of statins and fribrates. The composition according to the invention may therefore further comprise firbrates, and optionally statins.

In another embodiment, compositions of the invention may contain one or more antisense compounds, particularly oligonucleotides, targeted to a first nucleic acid and one or more additional antisense compounds targeted to a second nucleic acid target.

In a method according to the invention two or more combined compounds may be used together or sequentially.

The invention also provides pharmaceutical compositions which comprise oligomeric compounds according to the invention and further compounds capable of modulating blood serum cholesterol levels, such as PCSK9 modulators, in particular antisense oligonucleotides (oligomers) targeted to PCSK9 nucleic acid targets—such as those disclosed in PCT/EP2007/060703, hereby incorporated by reference.

The invention also provides pharmaceutical compositions which comprise oligomeric compounds according to the invention and further compounds capable of modulating blood serum cholesterol levels, such as FABP4 modulators, in particular antisense oligonucleotides (oligomers) targeted to FABP4 nucleic acid targets—such as those disclosed in U.S. provisional application 60/969,016, hereby incorporated by reference.

Applications

Further provided are methods of modulating the expression of apolipoprotein B in cells or tissues comprising contacting said cells or tissues with one or more of the oligonucleotide compounds or compositions of the invention. Also disclosed are methods of treating an animal or a human, suspected of having or being prone to a disease or condition, associated with expression of apolipoprotein B by administering a therapeutically or prophylactically effective amount of one or more of the oligonucleotide compounds or compositions of the invention. Further, methods of using oligonucleotide compounds for the inhibition of expression of apolipoprotein B and for treatment of diseases associated with apolipoprotein B activity are provided. Examples of such diseases are different types of HDL/LDL cholesterol imbalance; dyslipidemias, e.g., familial combined hyperlipidemia (FCHL), acquired hyperlipidemia, hypercholestorolemia; statin-resistant hypercholesterolemia; coronary artery disease (CAD) coronary heart disease (CHD) atherosclerosis.

The invention further provides for the use of a compound or as conjugate as defined herein for the manufacture of a medicament for the treatment of abnormal levels of Apo-B100 or a disease or condition correlated thereto.

The invention further provides for a medicament comprising the compound or conjugate according to the invention for the treatment of abnormal levels of Apo-B100 or a disease or condition correlated thereto.

In one embodiment, the diseases and conditions correlated to abnormal levels of Apo-B100 may be selected from the group consisting of: atherosclerosis, hypercholesterolemia or hyperlipidemia.

The invention further provides for a method of treating a subject suffering from a disease or condition selected from atherosclerosis, hypercholesterolemia and hyperlipidemia, the method comprising the step of administering a pharmaceutical composition or conjugate as defined herein to the subject in need thereof.

The invention further provides for a method for downregulation apolipoprotein B, the method comprising the step of administering a pharmaceutical composition or conjugate as defined herein to a subject, such as the subject suffering from a medical condition selected from the group consisting of: atherosclerosis, hypercholesterolemia or hyperlipidemia.

Salts

The Oligomeric compound can be employed in a variety of pharmaceutically acceptable salts. As used herein, the term refers to salts that retain the desired biological activity of the LNA oligonucleotide and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or combinations, e.g., a zinc tannate salt or the like.

Such salts are formed, from the Oligomeric compound which possess phosphorodiester group and/or phosphorothioate groups, and are, for example, salts with suitable bases. These salts include, for example, nontoxic metal salts which are derived from metals of groups Ia, Ib, IIa and IIb of the Periodic System of the elements, in particular suitable alkali metal salts, for example lithium, sodium or potassium salts, or alkaline earth metal salts, for example magnesium or calcium salts. They furthermore include zinc and ammonium salts and also salts which are formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl) amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts. Lithium salts, sodium salts, magnesium salts, zinc salts or potassium salts are preferred, with sodium salts being particularly preferred.

Prodrugs

In one embodiment, the LNA oligonucleotide may be in the form of a prodrug. Oligonucleotides are by virtue negatively charged ions. Due to the lipophilic nature of cell membranes, the cellular uptake of oligonucleotides is reduced compared to neutral or lipophilic equivalents. This polarity "hindrance" can be avoided by using the prodrug approach (see e.g. Crooke, R. M. (1998) in Crooke, S. T. *Antisense research and Application*. Springer-Verlag, Berlin, Germany, vol. 131, pp. 103-140). In this approach, the Oligomeric compound are prepared in a protected manner so that the Oligomeric compound are neutral when it is administered. These protection groups are designed in such a way that they can be removed when the LNA oligonucleotide is taken up by the cells. Examples of such protection groups are S-acetylthioethyl (SATE) or S-pivaloylthioethyl (t-butyl-SATE). These protection groups are nuclease resistant and are selectively removed intracellulary.

EMBODIMENTS OF THE INVENTION

The following embodiments may be combined with the features of the invention as referred to herein:

1. An oligomeric compound consisting of a total of 10-15 nucleobases, wherein the nucleobase sequence of said compound is present in SEQ ID NO 1, wherein said compound comprises at least 2 or at least 3 nucleotide analogues.

2. The compound according to embodiment 1, wherein the nucleobase sequence comprises, in a 5' to 3' direction i) region A: a stretch of 2-4 nucleotide analogues, followed by ii) region B: a stretch of 6-11 nucleotides (such as DNA nucleotides), which is followed by iii) region C: a stretch of 2-4 nucleotide analogues, and optionally iv) one or two nucleotides (D).

3. The compound according to embodiment 2, wherein region A has a length of 2 nucleotide analogues.

4. The compound according to embodiment 2, wherein region A has a length of 3 nucleotide analogues.

5. The compound according to embodiment 2, wherein region A has a length of 4 nucleotide analogues.

6. The compound according to any one of embodiments 2-5, wherein region C has a length of 2 nucleotide analogues.

7. The compound according to any one of embodiments 2-5, wherein region C has a length of 3 nucleotide analogues.

8. The compound according to any one of embodiments 2-5, wherein region C has a length of 4 nucleotide analogues.

9. The compound according to any one of embodiments 2-8, wherein region B has a length of between 7 and 10 nucleotides (such as DNA nucleotides), such as 8 or 9 nucleotides (such as DNA nucleotides).

10. The compound according to any one of the preceding embodiments which has a length of from 12-15 nucleobases.

11. The compound according to embodiment 10 which has a length of 12, 13, or 14 nucleobases.

12. The compound according to any one of the preceding embodiments, wherein said nucleobase sequence comprises a internucleobase linkage group selected from the group consisting of a phosphate group, a phosphodiester group, a phosphorothioate group and a boranophosphate group, the internucleoside linkage may be —O—P(O)$_2$—O—, —O—P(O, S)—O—.

13. The compound according to any one of embodiments 1-12, wherein the internucleobase linkage groups between the nucleobase units of the nucleobase sequence are independently selected from either phosphorothioate or phosphodiester linkage groups.

14. The compound according to embodiment 12 or 13, wherein the region A comprises at least one phosphodiester linkage between two nucleotide analogue units, or a nucleotide analogue unit and a nucleotide unit.

15. The compound according to any one of embodiments 12-14, wherein region C comprises at least one phosphodiester linkage between two nucleotide analogue units, or a nucleotide analogue unit and a nucleotide unit.

16. The compound according to any one of embodiments 12-15, wherein the internucleotide linkages between the nucleotides of region B are phosphorothioate.

17. The compound according to any one of embodiments 12-16 wherein the internucleobase linkage between the 3' nucleotide analogue of A and the 5' nucleotide of region B is a phosphorothioate.

18. The compound according to any one of embodiments 12-17 wherein the internucleobase linkage between the 3' nucleotide of region B and the 5' nucleotide analogue of region C is a phosphorothioate.

19. The compound according to any one of embodiments 10-16 and 18 wherein the internucleobase linkage between the 3' nucleotide analogue of A and the 5' nucleotide of region B is a phosphodiester.

20. The compound according to any one of embodiments 10-17 and 19 wherein the internucleobase linkage between the 3' nucleotide of region B and the 5' nucleotide analogue of region C is a phosphodiester.

21. The compound according to any one of embodiments 12-20, wherein the internucleobase linkage between the two 5' nucleotide analogues of region A are phosphodiester.

22. The compound according to any one of embodiments 12-21, wherein the internucleobase linkage between the two 3' nucleotide analogues of region C are phosphodiester.

23. The compound according to any one of embodiments 12-22, wherein the internucleobase linkage between the two 3' nucleotide analogues of region A are phosphodiester.

24. The compound according to any one of embodiments 12-23, wherein the internucleobase linkage between the two 5' nucleotide analogues of region C are phosphodiester.

25. The compound according to any one of embodiments 12-24, wherein region A has a length of 4 nucleotide analogues and internucleobase linkage between the two middle nucleotide analogues of region A are phosphodiester.

26. The compound according to any one of embodiments 12-25, wherein region C has a length of 4 nucleotide analogues and internucleobase linkage between the two middle nucleotide analogues of region C are phosphodiester.

27. The compound according to any one of embodiments 10-26 wherein all the internucleobase linkages between nucleotide analogues are phosphodiester.

28. The compound according to any one of embodiments 10-27 wherein all remaining internucleobase linkages are either phosphodiester or phosphorothioate.

29. The compound according to embodiment 12, wherein all the internucleobase linkage groups are phosphorothioate.

30. The compound according to any one of embodiments 1-29 wherein the nucleotide analogues are independently selected from the group consisting of: 2'-O-alkyl-RNA monomers, 2'-amino-DNA monomers, 2'-fluoro-DNA monomers, LNA monomers, arabino nucleic acid (ANA) monomers, 2'-fluoro-ANA monomers, HNA monomers, INA monomers.

31. The compound according to embodiment 30 wherein the nucleotide analogues are independently selected from the group consisting of 2'-MOE-RNA (2'-O-methoxyethyl-RNA), 2'Fluoro-DNA, and LNA.

32. The compound according to embodiment 30 or 31 wherein at least one of said nucleotide analogues is a locked nucleic acid (LNA).

33. The compound according to any one of embodiments 30-32 wherein at least one of said nucleotide analogues is 2'-MOE-RNA, such as 2, 3, 4, 5, 6, 7 or 8 2'-MOE-RNA nucleobase units.

34. The compound according to any one of embodiments 30-33 wherein at least one of said nucleotide analogues is 2'-fluoro DNA, such as 2, 3, 4, 5, 6, 7 or 8 2'-fluoro-DNA nucleobase units.

35. The compound according to any one of embodiments 30-34 wherein 2, 3, 4, 5, 6, 7 or 8 of the nucleotide analogues are LNA and any remaining nucleotide analogue may be selected from the groups of nucleotide analogues referred to any one of embodiments 26-30.

36. The compound according to embodiment 32 wherein all the nucleotide analogues are LNA.

37. The compound according to any one of embodiments 30-36 wherein LNA is selected from beta-D-oxy-LNA, alpha-L-oxy-LNA, beta-D-amino-LNA and beta-D-thio-LNA.

38. The compound according to any one of embodiments 1-37, wherein the nucleobase sequence selected from the group consisting of SEQ ID NOS 2, 3, 4, 5, 6, 7, 8, 9, 10, 11, 12, 13, 14, 15.

39. The compound according to embodiment 38, which is selected from the group consisting of SEQ ID NO: 17, 18, 19, 20, 21, 22, 23, 24 and 25.

40. The compound according to embodiment 38, which is selected from the group consisting of SEQ ID NO: 26, 27, 28, 29, 30, 31, 32, and 33.

41. The compound according to embodiment 38, which is selected from the group consisting of SEQ ID NO 34, 35, 36, 37, 38, 39 and 40.

42. A conjugate comprising the compound according to any one of the embodiments 1-41 and at least one non-nucleotide or non-polynucleotide moiety covalently attached to said compound.

43. A conjugate according to embodiment 42 wherein said non-nucleotide or non-polynucleotide moiety consists or comprise a sterol group such as cholesterol.

44. A pharmaceutical composition comprising a compound as defined in any one of the embodiments 1-40 or a conjugate as defined in embodiment 42 or 43, and a pharmaceutically acceptable diluent, carrier or adjuvant.

45. The pharmaceutical composition according to embodiment 44 further comprising at least one cholesterol-lowering compound.

46. The pharmaceutical composition according to embodiment 45, wherein said compound is selected from the group consisting of bile salt sequestering resins (e.g., cholestyramine, colestipol, and colesevelam hydrochloride), HMGCoA-reductase inhibitors (e.g., lovastatin, cerivastatin, prevastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), implitapide, inhibitors of bile acid transporters (apical sodium-dependent bile acid transporters), regulators of hepatic CYP7a, estrogen replacement therapeutics (e.g., tamoxifen), and anti-inflammatories (e.g., glucocorticoids).

47. A compound or a conjugate as defined in any one of embodiments 1-43 for use as a medicament.

48. Use of a compound or as conjugate as defined in any one of embodiments 1-43 for the manufacture of a medicament for the treatment of abnormal levels of Apo-B100 or a disease or condition correlated thereto.

49. A medicament comprising the compound or conjugate according to any one of embodiments 1-43, for the treatment of abnormal levels of Apo-B100 or a disease or condition correlated thereto.

50. The use or medicament according to embodiments 48 or 49, wherein said abnormal levels of Apo-B100 is correlated to the presence of a medical condition selected from the group consisting of: atherosclerosis, hypercholesterolemia or hyperlipidemia.

51. A method of treating a subject suffering from a disease or condition selected from atherosclerosis, hypercholesterolemia and hyperlipidemia, the method comprising the step of administering a pharmaceutical composition or conjugate as defined in any one of the embodiments 1-43 to the subject in need thereof.

52. A method for down-regulation apolipoprotein B, the method comprising the step of administering a pharmaceutical composition or conjugate as defined in any one of the embodiments 1-43 to a subject, such as the subject suffering from a medical condition selected from the group consisting of: atherosclerosis, hypercholesterolemia or hyperlipidemia.

EXAMPLES

Example 1

Monomer Synthesis

The LNA monomer building blocks and derivatives thereof were prepared using standard methods, such as the published procedures and references cited in WO07/031,081.

Example 2

Oligonucleotide Synthesis

TABLE 1

Oligonucleotide compound of the invention

| Test substance | Sequence | Size | |
|---|---|---|---|
| SEQ ID NO: 1 | 5'-CAGC ATTG GTAT TCAG-3' | 16 | Antisense motif |
| SEQ ID NO: 2 | 5'-CAGC ATTG GTAT TCA-3' | 15 | Antisense motif |
| SEQ ID NO: 3 | 5'-AGCA TTGG TATT CAG-3' | 15 | Antisense motif |
| SEQ ID NO: 4 | 5'-CAGC ATTG GTAT TC-3' | 14 | Antisense motif |
| SEQ ID NO: 5 | 5'-AGCA TTGG TATT CA-3' | 14 | Antisense motif |
| SEQ ID NO: 6 | 5'-GCAT TGGT ATTC AG-3' | 14 | Antisense motif |
| SEQ ID NO: 7 | 5'-CAGC ATTG GTAT T-3' | 13 | Antisense motif |
| SEQ ID NO: 8 | 5'-AGCA TTGG TATT C-3' | 13 | Antisense motif |
| SEQ ID NO: 9 | 5'-GCAT TGGT ATTC A-3' | 13 | Antisense motif |
| SEQ ID NO: 10 | 5'-CATT GGTA TTCA G-3' | 13 | Antisense motif |
| SEQ ID NO: 11 | 5'-CAGC ATTG GTAT-3' | 12 | Antisense motif |
| SEQ ID NO: 12 | 5'-AGCA TTGG TATT-3' | 12 | Antisense motif |
| SEQ ID NO: 13 | 5'-GCAT TGGT ATTC-3' | 12 | Antisense motif |
| SEQ ID NO: 14 | 5'-CATT GGTA TTCA-3' | 12 | Antisense motif |
| SEQ ID NO: 15 | 5'-ATTG GTAT TCAG-3' | 12 | Antisense motif |
| SEQ ID NO: 16 | 5'-$A_s G_s^{Me} C_s a_s t_s t_s g_s g_s t_s a_s t_s T_s^{Me} C_s A_s g$-3' | 16 | Motif #1 |
| SEQ ID NO: 17 | 5'-$A_s G_s^{Me} C_s a_s t_s t_s g_s g_s t_s a_s t_s T_s^{Me} C_s A$-3' | 14 | Motif #5 |
| SEQ ID NO: 18 | 5'-$A G_s^{Me} C_s a_s t_s t_s g_s g_s t_s a_s t_s T_s^{Me} C_s A$-3' | 14 | Motif #5 |
| SEQ ID NO: 19 | 5'-$A_s G^{Me} C_s a_s t_s t_s g_s g_s t_s a_s t_s T_s^{Me} C_s A$-3' | 14 | Motif #5 |
| SEQ ID NO: 20 | 5'-$A_s G_s^{Me} C a_s t_s t_s g_s g_s t_s a_s t_s T_s^{Me} C_s A$-3' | 14 | Motif #5 |
| SEQ ID NO: 21 | 5'-$A_s G_s^{Me} C_s a_s t_s t_s g_s g_s t_s a_s t T_s^{Me} C_s A$-3' | 14 | Motif #5 |
| SEQ ID NO: 22 | 5'-$A_s G_s^{Me} C_s a_s t_s t_s g_s g_s t_s a_s t_s T^{Me} C_s A$-3' | 14 | Motif #5 |
| SEQ ID NO: 23 | 5'-$A_s G_s^{Me} C_s a_s t_s t_s g_s g_s t_s a_s t_s T^{Me}_s C A$-3' | 14 | Motif #5 |

TABLE 1-continued

Oligonucleotide compound of the invention

| Test substance | Sequence | Size | |
|---|---|---|---|
| SEQ ID NO: 24 | 5'-AG$_s^{Me}$C$_s$a$_s$t$_s$t$_s$g$_s$g$_s$t$_s$a$_s$t$_s$T$_s^{Me}$CA-3' | 14 | Motif #5 |
| SEQ ID NO: 25 | 5'-AG$^{Me}$C$_s$a$_s$t$_s$t$_s$g$_s$g$_s$t$_s$a$_s$t$_s$T$^{Me}$CA-3' | 14 | Motif #5 |
| SEQ ID NO: 26 | 5'-G$_s^{Me}$C$_s$a$_s$t$_s$t$_s$g$_s$g$_s$t$_s$a$_s$t$_s$T$_s^{Me}$C$_s$A-3' | 13 | Motif #9 |
| SEQ ID NO: 27 | 5'-G$^{Me}$C$_s$a$_s$t$_s$t$_s$g$_s$g$_s$t$_s$a$_s$t$_s$T$_s^{Me}$C$_s$A-3' | 13 | Motif #9 |
| SEQ ID NO: 28 | 5'-G$_s^{Me}$C a$_s$t$_s$t$_s$g$_s$g$_s$t$_s$a$_s$t$_s$T$_s^{Me}$C$_s$A-3' | 13 | Motif #9 |
| SEQ ID NO: 29 | 5'-G$_s^{Me}$C$_s$a$_s$t$_s$t$_s$g$_s$g$_s$t$_s$a$_s$t$_s$T$_s^{Me}$C$_s$A-3' | 13 | Motif #9 |
| SEQ ID NO: 30 | 5'-G$_s^{Me}$C$_s$a$_s$t$_s$t$_s$g$_s$g$_s$t$_s$a$_s$t$_s$T$^{Me}$C$_s$A-3' | 13 | Motif #9 |
| SEQ ID NO: 31 | 5'-G$_s^{Me}$C$_s$a$_s$t$_s$t$_s$g$_s$g$_s$t$_s$a$_s$t$_s$T$_s^{Me}$CA-3' | 13 | Motif #9 |
| SEQ ID NO: 32 | 5'-G$^{Me}$C$_s$a$_s$t$_s$t$_s$g$_s$g$_s$t$_s$a$_s$t$_s$T$_s^{Me}$CA-3' | 13 | Motif #9 |
| SEQ ID NO: 33 | 5'-G$^{Me}$C$_s$a$_s$t$_s$t$_s$g$_s$g$_s$t$_s$a$_s$t$_s$T$^{Me}$CA-3' | 13 | Motif #9 |
| SEQ ID NO: 34 | 5'-G$_s^{Me}$C$_s$a$_s$t$_s$t$_s$g$_s$g$_s$t$_s$a$_s$t$_s$T$_s^{Me}$C-3' | 12 | Motif #13 |
| SEQ ID NO: 35 | 5'-G$^{Me}$C$_s$a$_s$t$_s$t$_s$g$_s$g$_s$t$_s$a$_s$t$_s$t$_s$T$_s^{Me}$C-3' | 12 | Motif #13 |
| SEQ ID NO: 36 | 5'-G$_s^{Me}$C a$_s$t$_s$t$_s$g$_s$g$_s$t$_s$a$_s$t$_s$T$_s^{Me}$C-3' | 12 | Motif #13 |
| SEQ ID NO: 37 | 5'-G$_s^{Me}$C$_s$a$_s$t$_s$t$_s$g$_s$g$_s$t$_s$a$_s$t$_s$T$_s^{Me}$C-3' | 12 | Motif #13 |
| SEQ ID NO: 38 | 5'-G$_s^{Me}$C$_s$a$_s$t$_s$t$_s$g$_s$g$_s$t$_s$a$_s$t$_s$T$^{Me}$C-3' | 12 | Motif #13 |
| SEQ ID NO: 39 | 5'-G$^{Me}$C$_s$a$_s$t$_s$t$_s$g$_s$g$_s$t$_s$a$_s$t$_s$T$^{Me}$C-3' | 12 | Motif #13 |
| SEQ ID NO: 40 | 5'-G$^{Me}$C a$_s$t$_s$t$_s$g$_s$g$_s$t$_s$a$_s$t$T$^{Me}$C-3' | 12 | Motif #13 |
| SEQ ID NO: 41 | 5'-$^m$C$_s^o$A$_s^o$G$_s^o$ c$_s$ a$_s$ t$_s$ t$_s$ g$_s$ g$_s$ t$_s$ a$_s$ t$_s$ T$_s^o$$^m$C$_s^o$A$^o$-3' | 15 | Motif #2 |
| SEQ ID NO: 42 | 5'-A$_s^o$G$_s^o$ c$_s$ a$_s$ t$_s$ t$_s$ g$_s$ g$_s$ t$_s$ a$_s$ t$_s$ T$_s^o$$^m$C$_s^o$ a-3' | 14 | Motif #5 |
| SEQ ID NO: 43 | 5'-A$_s^o$G$_s^o$ c$_s$ a$_s$ t$_s$ t$_s$ g$_s$ g$_s$ t$_s$ a$_s$ T$_s^o$T$_s^o$$^m$C$_s^o$ a-3' | 14 | Motif #5 |
| SEQ ID NO: 44 | 5'-A$_s^o$G$_s^o$$^m$C$_s^o$ a$_s$ t$_s$ t$_s$ g$_s$ g$_s$ t$_s$ a$_s$ T$_s^o$T$_s^o$$^m$C$_s^o$ a-3' | 14 | Motif #5 |
| SEQ ID NO: 45 | 5'-G$_s^o$ c$_s$ a$_s$ t$_s$ t$_s$ g$_s$ g$_s$ t$_s$ a$_s$ t$_s$ T$_s^o$$^m$C$^o$ -3' | 12 | Motif #13 |
| SEQ ID NO: 46 | 5'-G$_s^o$$^m$C$_s^o$ a$_s$ t$_s$ t$_s$ g$_s$ g$_s$ t$_s$ a$_s$ T$_s^o$T$_s^o$$^m$C$^o$-3' | 12 | Motif #13 |
| SEQ ID NO: 47 | 5'-G$_s^o$ c$_s$ a$_s$ t$_s$ t$_s$ g$_s$ g$_s$ t$_s$ a$_s$ T$^o$-3' | 10 | |
| SEQ ID NO: 48 | 5'-G$_s^o$$^m$C$_s^o$ a$_s$ t$_s$ t$_s$ g$_s$ g$_s$ t$_s$ A$_s^o$T$^o$-3' | 10 | |
| SEQ ID NO: 49 | 5'-G$_s^o$$^m$C$_s^o$ a$_s$ t$_s$ t$_s$ g$_s$ g$_s$ T$_s^o$A$_s^o$T$^o$-3' | 10 | |

In SEQ ID NOS: 16-40, upper case letters indicates nucleotide analogue units and subscript "$_s$" represents phosphorothiote linkage. Absence of "s" indicates phosphodiester linkage.

Example 3

Cholesterol Levels in Plasma

Total cholesterol level is measured in plasma using a colometric assay Cholesterol CP from ABX Pentra. The cholesterol is measured following enzymatic hydrolysis and oxidation. 21.5 µL water was added to 1.5 µL plasma. 250 µL reagent is added and within 5 min the cholesterol content is measured at a wavelength of 540 nM. Measurements on each animal was made in duplicates. The sensitivity and linearity was tested with 2 fold diluted control compound (ABX Pentra N control). The relative Cholesterol level was determined by subtraction of the background and presented relative to the cholesterol levels in plasma of saline treated mice.

Lipoproteins in plasma were separated in HDL and non-HDL fractions from density adjusted plasma by ultracentrifugation. The non-HDL fraction primarily contains VLDL and LDL. Cholesterol content in each of the two fractions was analysed using a commercial kit for total cholesterol from ABX Diagnostics, France as described for total cholesterol analysis.

Example 4

Measurements of mRNA Levels

Antisense modulation of Apo-B100 expression can be assayed in a variety of ways known in the art. For example, Apo-B100 mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA. Methods of RNA isolation and RNA analysis such as Northern blot analysis is routine in the art and is taught in, for example, Current Protocols in Molecular Biology, John Wiley and Sons.

Real-time quantitative (PCR) can be conveniently accomplished using the commercially iQ Multi-Color Real Time PCR Detection System available from BioRAD. Real-time Quantitative PCR is a technique well known in the art and is taught in for example Heid et al. Real time quantitative PCR, Genome Research (1996), 6: 986-994.

Example 5

Screening of Oligonucleotides Targeting ApoB-100 mRNA (Dosing 3*5 mg/kg)

In this study 5 mg/kg/dose were dosed on 3 consecutive days (one dose/day i.v.) and animals were sacrificed 24 hours after last dosing. At sacrifice, liver and retro orbital sinus blood was sampled. Serum was prepared from blood for analysis of cholesterol. RNA was isolated from the liver and the expression of ApoB-100 mRNA was measured.

The effect of dosing three doses at 5 mg/kg/dose of oligos of different length on ApoB-100 mRNA expression is shown in FIG. 1. SEQ ID NO 16 down regulated ApoB-100 mRNA with about 25-30%, whereas the 14-mer SEQ ID NO 17 and 12-mer SEQ ID NO 34 was much more potent and equally potent—down regulated ApoB-100 mRNA with about 75% after dosing 3 times 5 mg/kg.

Figure 2:
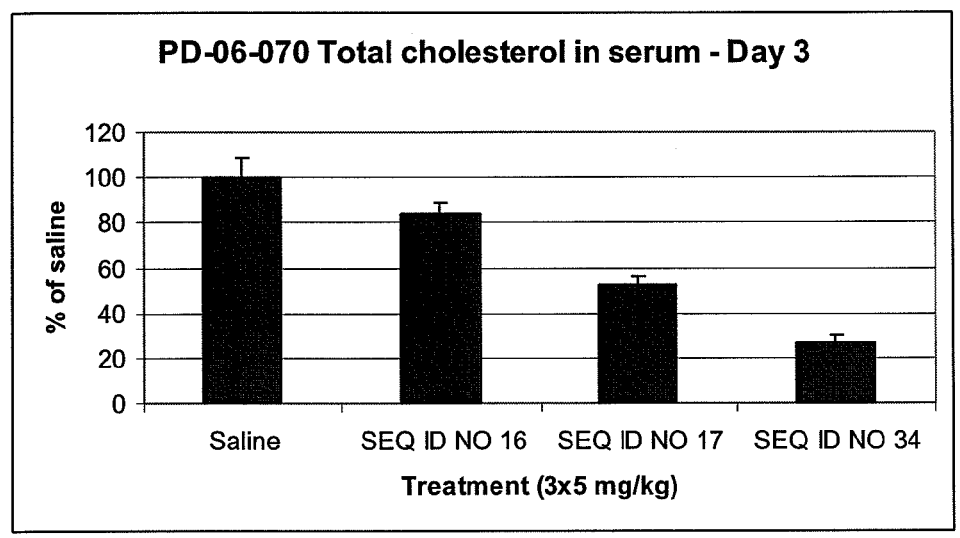
FIG. 2. Serum cholesterol levels at sacrifice (day 3) after dosing oligoes of different length.

Total cholesterol was measured in serum at sacrifice, day 3 (FIG. 2). Similar to the results from the qPCR the best or the most potent effect was obtained with the 12-mer SEQ ID NO 34 followed by the 14-mer SEQ ID NO 17. The 16-mer (SEQ ID NO 16) reduced total cholesterol with about 18%.

Example 6

Dose Response and Duration of Action of SEQ ID NO 17 and SEQ ID NO 34 in C57BL/6 Female Mice In this study three different concentrations (10, 15 and 25 mg/kg) of SEQ ID NO 17 and SEQ ID NO 34 were examined for duration of action on ApoB-100 mRNA expression and serum cholesterol level. SEQ ID NO 17 and SEQ ID NO 34 were given as a single dose of 10, 15 or 25 mg/kg to C57BL/6 female mice. Mice were sacrificed at different time points (1, 3, 5 and 8 days) after dosing; liver and serum were examined for ApoB-100 mRNA expression, liver oligonucleotide concentration and cholesterol and ALT, respectively.

Analysis of Target mRNA Down Regulation

Figure 3:
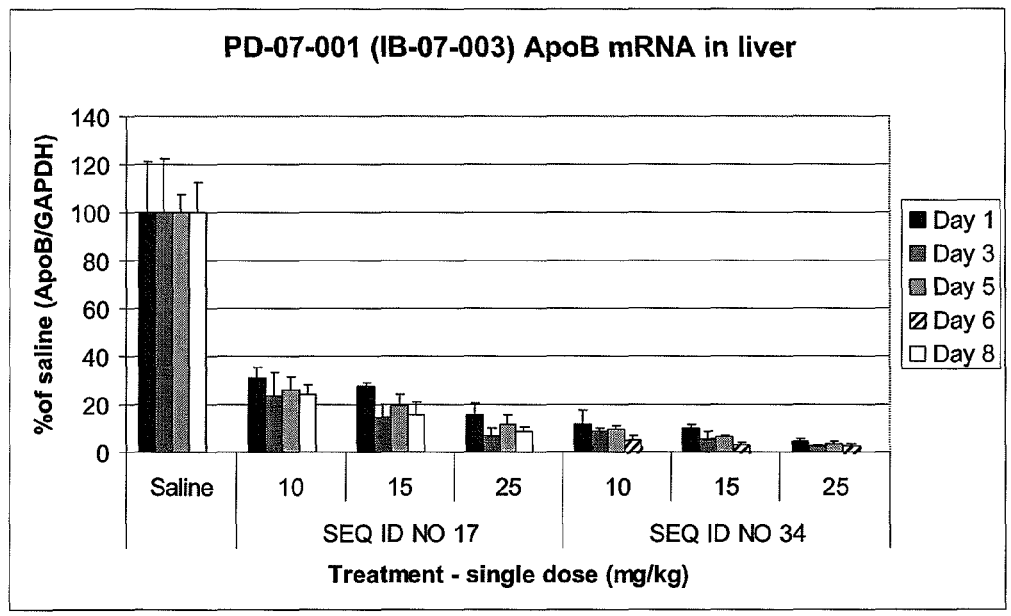
FIG. 3. The apoB-100 mRNA expression was measured by qPCR normalized to the house keeping gene GAPDH and presented relative to the saline group. Mice (n=5) were dosed once and sacrifice different days after dosing, liver was isolated and analysed.

Liver sampled at sacrifice was analysed for ApoB-100 mRNA expression by qPCR. Data was normalized to Gapdh and presented relative to the data obtained by dosing saline. One dose of 10, 15 or 25 mg/kg of SEQ ID NO 17 or SEQ ID NO 34 was very effective to down regulate ApoB-100 mRNA in liver (FIG. 3). Twenty-four hours after dosing, down regulation of 90-95% was obtained with SEQ ID NO 34, whereas dosing of SEQ ID NO 17 resulted in 70-85% lower ApoB mRNA levels than in the saline control group.

Serum Cholesterol

Figure 4:
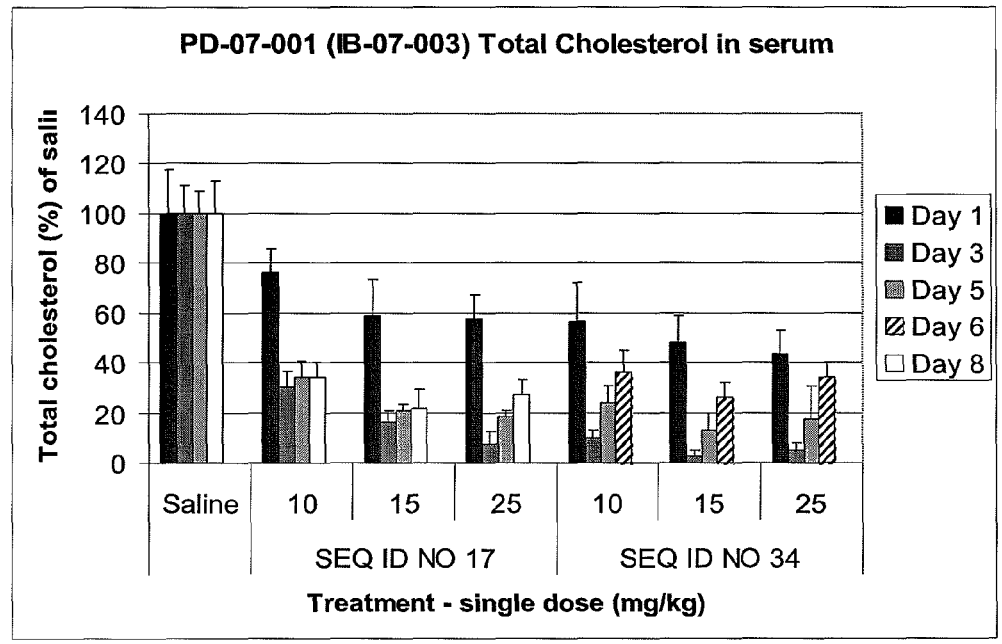
FIG. 4. Serum total cholesterol measured at sacrifice (days 1, 3, 5, 6 and 8) using a ABX pentra kit., n=5.

Blood serum used to measure cholesterol was sampled at sacrifice. Twenty-four hours after dosing SEQ ID NO 17 serum total cholesterol was reduced 25-40%, and dosing SEQ ID NO 34 gave 40-55% reduction in total cholesterol. At day 3, the total cholesterol level was further reduced: SEQ ID NO 17 gave 70-90% reduction in a dose dependent manner after doing 10, 15 or 25 mg/kg. SEQ ID NO 34 reduced total cholesterol with 90-95% relative to the saline control group. At day 5-8 the total cholesterol level increased in all groups except the group dosed SEQ ID NO 17 at 10 mg/kg. (FIG. 4.).

Example 7

Dose Response and Duration of Action of SEQ ID NO 17 and SEQ ID NO 34 in C57BL/6 Female Mice A single dose of SEQ ID NO 17 and SEQ ID NO 34 at different concentrations was administered to C57BL/6J mice to find ED50 values for cholesterol. Duration of action was also included in this study, because we previously have seen that maximum effect of a single dose not always was achieved 24 hours after dosing. In Example 6, we completely down-regulated ApoB-100 mRNA after dosing 10, 15 or 25 mg/kg SEQ ID NO 34 and 25 mg/kg SEQ ID NO 17. In this study we therefore have chosen lower concentrations (1, 2.5 and 5 mg/kg).

Analysis of Target mRNA Down Regulation

Figure 5:
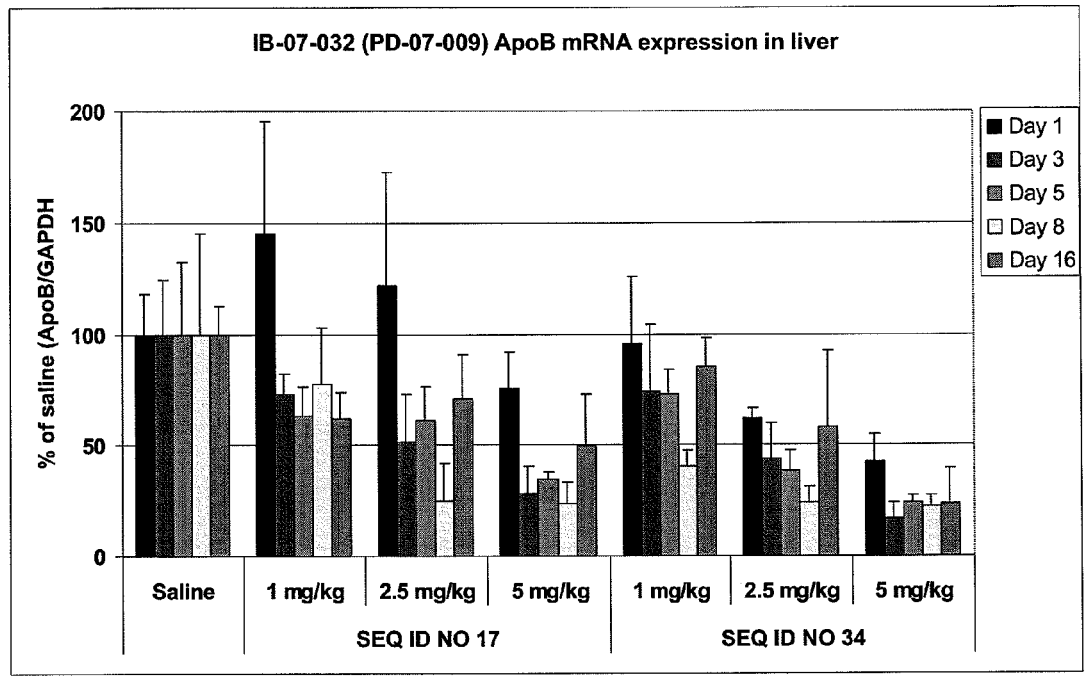
FIG. 5. The apoB-100 mRNA expression was measured by qPCR normalized to the house keeping gene GAPDH and presented relative to the saline group. Mice (n=5) were dosed once and sacrifice different days after dosing, liver was isolated and analysed.
Figure 6:
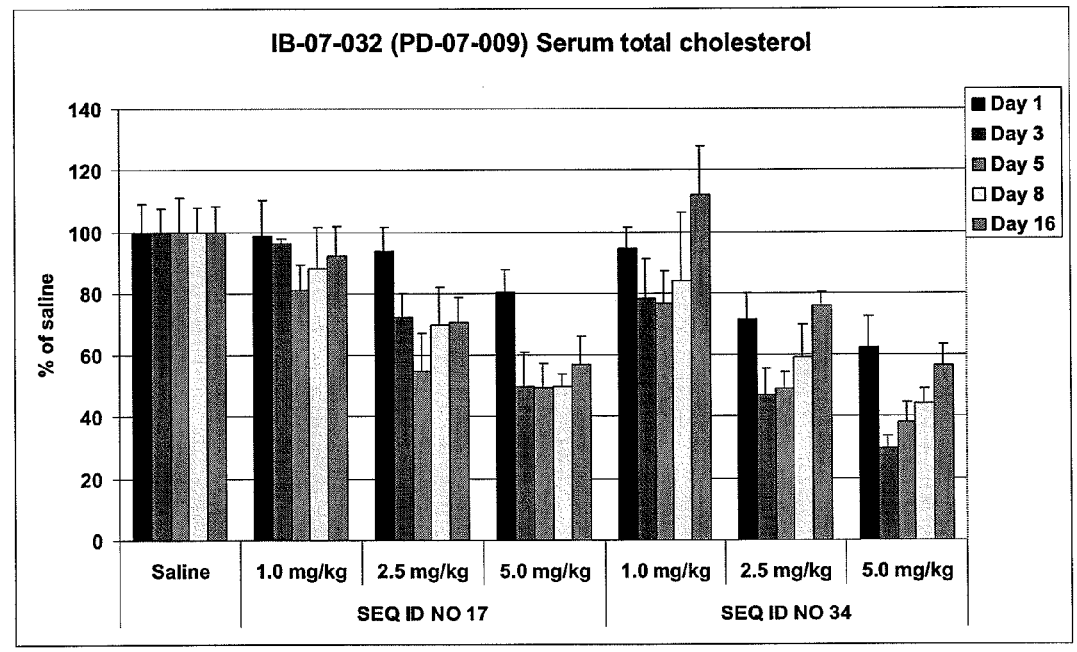
FIG. 6. Serum total cholesterol measured at sacrifice (days 1, 3, 5, 6, 8 and 16) using a ABX pentra kit., n=5.

Liver sampled at sacrifice was analyzed for ApoB-100 mRNA expression by qPCR. Data was normalized to Gapdh and presented relative to the data obtained by dosing saline. One dose of 10, 15 or 25 mg/kg of SEQ ID NO 17 or SEQ ID NO 34 was very effective to down regulate ApoB-100 mRNA in liver (FIG. 5). A single dose of SEQ ID NO 17 of 1, 2.5 or 5 mg/kg resulted in a dose dependent down regulation of ApoB-100 mRNA with a duration of 5 days. Similar results were obtained with SEQ ID NO 34. At day 8 both oligonucleotides resulted in ApoB-100 mRNA expression that was similar after dosing 2.5 SEQ ID NO 34 and 5 mg/kg SEQ ID NO 17, reduction of 75%. At day 16 the mRNA level had increased again in all groups, except after dosing 5 mg/kg SEQ ID NO 34 with ApoB-100 mRNA down regulation of 75% similar to that at days 5 and 8.

Serum Cholesterol

Blood serum was sampled at sacrifice and used to measure cholesterol. The serum total cholesterol level reflected the mRNA expression of ApoB-100; dose dependent reduction with best effect at 5 days after dosing SEQ ID NO 17 at 1 and 2.5 mg/kg and similar effect at days 3, 5 and 8 after dosing 5 mg/kg (50% reduction). Dose dependent effect was also obtained after dosing SEQ ID NO 34 with best effect at day 3 after dosing 5 mg/kg (70% reduction) with following increase in cholesterol level (60% reduction at day 8 and 45% at day 16). However, the cholesterol levels in the groups dosed SEQ ID NO 34 did not follow the mRNA reductions in the groups dosed 2.5 and 5 mg/kg, e.g. dosing 5 mg/kg gave about 75% down regulation of ApoB-100 mRNA days 5-16 whereas the cholesterol level after dosing 2.5 mg/kg and 5 mg/kg increased from day 3 to day 16 from a 70% reduction to 45% reduction.

Example 8

Screening of Oligonucleotides Targeting ApoB-100 mRNA (Dosing 3 * 1 or 5 mg/kg i.v. Three Consecutive Days)

The effect on ApoB-100 mRNA was examined at different days after dosing 1.0 or 5.0 mg/kg (one dose day 0) of the three LNA antisense oligonucleotides 12-mer SEQ ID NO 34, SEQ ID NO 26 13-mer and 14-mer SEQ ID NO 17 all targeting ApoB mRNA.

Analysis of Target mRNA Down Regulation

Figure 7:
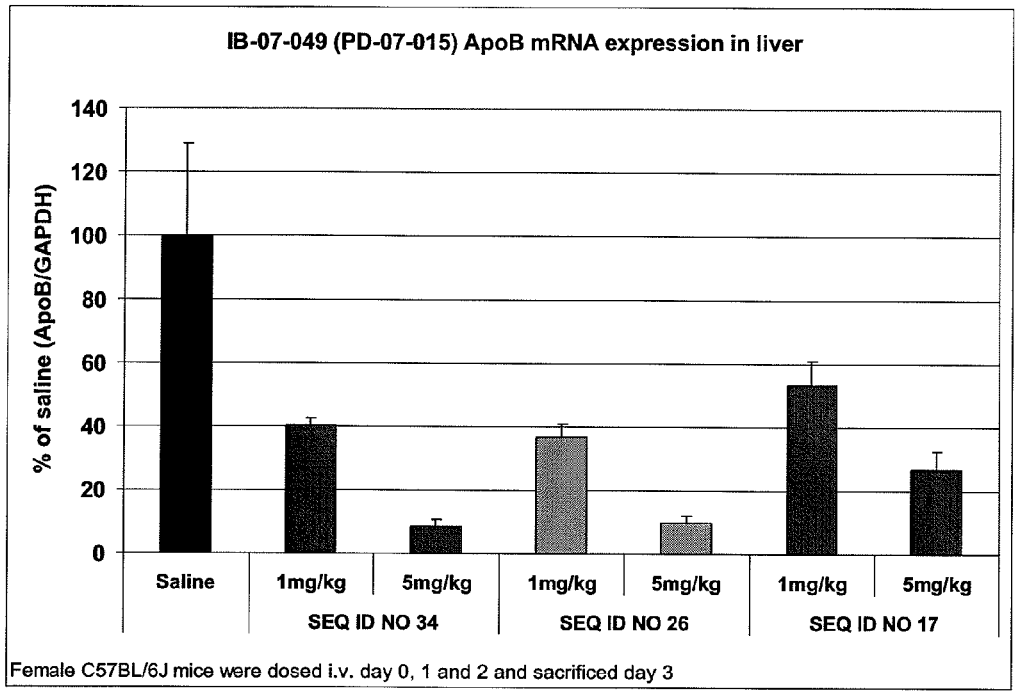
FIG. 7. The apoB-100 mRNA expression was measured by qPCR normalized to the house keeping gene GAPDH and presented relative to the saline group. Mice (n=5) were dosed 1 or 5 mg/kg 3 consecutive days and sacrificed 24 hours after last dosing (day 3), liver was isolated and analysed.
Figure 8:
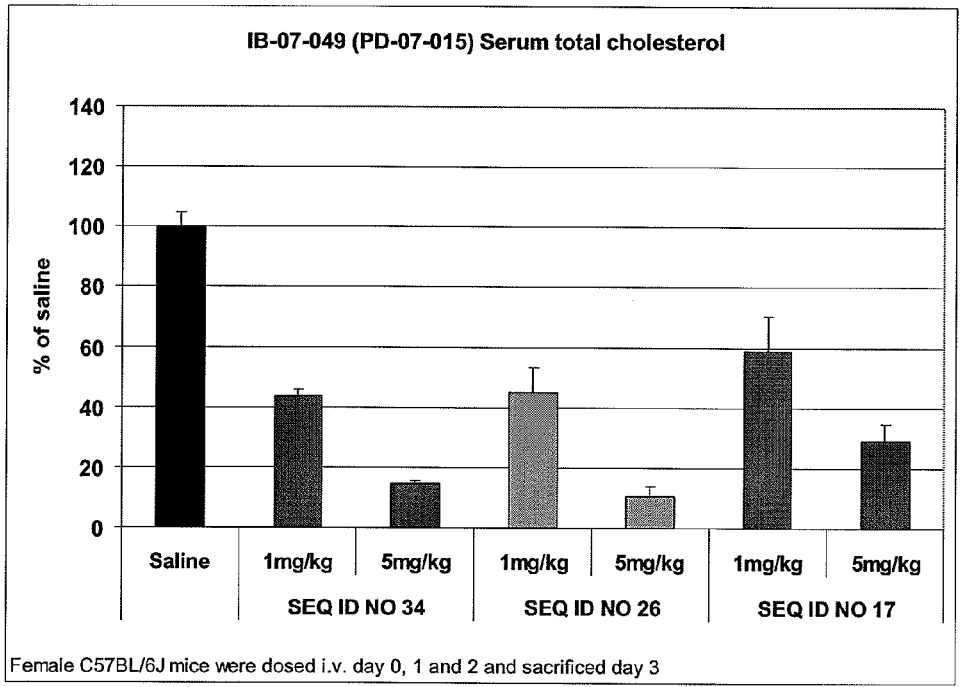
FIG. 8. Serum total cholesterol measured at sacrifice (day 3) using a ABX pentra kit., n=5.

Liver sampled at sacrifice was analyzed for ApoB-100 mRNA expression by qPCR. Data was normalized to Gapdh and presented relative to the data obtained by dosing saline. Dosing 3* 1 or 5 mg/kg of SEQ ID NO 34, SEQ ID NO 17 or SEQ ID NO 26 was very effective to down regulate ApoB-100 mRNA in liver (FIG. 7). Dosing 1 mg/kg SEQ ID NO 34 or SEQ ID NO 26 down regulated ApoB-100 mRNA with 60% and 5 mg/kg resulted in 90% down regulation similar for both compounds. SEQ ID NO 17 dosed 3* 1 mg/kg/dose or 5 mg/kg/dose down regulated target mRNA with 50% and 70% respectively.

Serum Cholesterol

At sacrifice blood for serum was sampled and used to measure cholesterol. Similar to the results for the mRNA expression, the SEQ ID NO 34 and SEQ ID NO 26 gave similar results: 60% reduction after dosing 3*1 mg/kg and about 85-90% after 3*5 mg/kg/dose. The SEQ ID NO 17 was a little less potent and reduced serum cholesterol with 40% and 70% after dosing 3* 1 or 5 mg/kg/dose, respectively.

Example 9

Dose Regimen and Efficacy of SEQ ID NO 26 in C57BL/6J Female Mice

In this study three different concentrations (1, 2.5 and 5 mg/kg) of SEQ ID NO 26 were examined for efficacy on total cholesterol as well as non-HDL and HDL cholesterol in lipoprotein fractions isolated from plasma by ultracentrifugation. SEQ ID NO 26 was given at 1, 2.5 or 5 mg/kg by intra venous injections to C57BL/6J female mice either once a week or once every two weeks for 6 weeks. Mice were sacrificed one week after the last dosing (day 42 for all groups). Serum was sampled once weekly and analyzed for total cholesterol as well as non-HDL and HDL cholesterol.

Plasma Cholesterol/Total Cholesterol

Blood Plasma used to measure cholesterol was sampled once weekly and at sacrifice.

Dosing once a week seemed to accumulate oligonucleotide in the liver because after 14 days the group dosed 2.5 and 5 mg/kg/dose has reached steady state with reduction of total cholesterol of 60%. Dosing 1 mg/kg resulted in steady state after 28 days with total cholesterol reduction of 40%. Dosing once every two weeks steady state without fluctuation was achieved after dosing 5 mg/kg/dose for 28 days (after 2 doses) with a reduction of 60% of total cholesterol. In the groups dosed 1 and 2.5 mg/kg fluctuations in total cholesterol continued until Day 35 after first dosing, however the fluctuation became smaller over time and it steady state at these concentrations would probably be established over time also at these concentrations. For 1 and 2.5 mg/kg/dose the reduction in total cholesterol fluctuated between 20-30% and 40-50%, respectively, from day 28 to 35 (FIG. 9 A and B).

Non-HDL and HDL Cholesterol

Dividing the plasma in HDL and non-HDL fractions and analyzed separately for cholesterol content, a difference between dosing once weekly (FIGS. 10 A and B) and once every two weeks was illuminated more clearly than when plasma samples were analyzed directly for total cholesterol content. FIGS. 11A and B illustrates that a bi-weekly dose regimen resulted in a lowering of non-HDL cholesterol levels that was almost comparable with the effect by weekly injections, whereas HDL cholesterol was more moderately affected by the bi-weekly regimen. It is noticeable that a bi-weekly injection was sufficient for lowering of non-HDL cholesterol, and results in a more favorable lipoprotein profile with higher HDL cholesterol, than weekly injections.

The invention claimed is:

1. An oligomeric compound 12, 13, or 14 nucleobases in length, wherein the nucleobase sequence of the compound is selected from the group consisting of SEQ ID NO:5, 9 and 13, and wherein said compound comprises at least 2 nucleotide analogues.

2. The compound according to claim 1, wherein the nucleobase sequence comprises, in a 5' to 3' direction, i) region A: a stretch of 2-4 nucleotide analogues, followed by ii) region B: a stretch of 6-11 nucleotides, which is followed by iii) region C: a stretch of 2-4 nucleotide analogues.

3. The compound according to claim 1, wherein the internucleobase linkage groups between the nucleobase units of the nucleobase sequence are independently selected from either phosphorothioate or phosphodiester linkage groups.

4. The compound of claim 1, wherein the nucleotide analogues are independently selected from the group consisting of: 2'-O-alkyl-RNA monomers, 2'-amino-DNA monomers, 2'-fluoro-DNA monomers, locked nucleic acid (LNA) monomers, arabino nucleic acid (ANA) monomers, 2'-fluoro-ANA monomers, D-hexitol nucleic acid (HNA) monomers, and intercalating nucleic acid (INA) monomers.

5. The compound according to claim 4 wherein at least one of said nucleotide analogues is a locked nucleic acid (LNA).

6. The compound according to claim 5 wherein all the nucleotide analogues are LNA.

7. The compound according to claim 5, wherein the LNA is selected from the group consisting of: beta-D-oxy-LNA, alpha-L-oxy-LNA, beta-D-amino-LNA and beta-D-thio-LNA.

8. The compound according to claim 1, which is selected from the group consisting of:

5'-$A_sG_s^{Me}C_sa_st_st_sg_sg_st_sa_st_sT_s^{Me}C_sA_sG$-3' (SEQ ID NO:17);
5'-$AG_s^{Me}C_sa_st_st_sg_sg_st_sa_st_sT_s^{Me}C_sA$-3' (SEQ ID NO:18);
5'-$A_sG^{Me}C_sa_st_st_sg_sg_st_sa_st_sT_s^{Me}C_sA$-3' (SEQ ID NO:19);
5'-$A_sG_s^{Me}Ca_st_st_sg_sg_st_sa_st_sT_s^{Me}C_sA$-3' (SEQ ID NO:20);
5'-$A_sG_s^{Me}C_sa_st_st_sg_sg_st_sa_stT_s^{Me}C_sA$-3' (SEQ ID NO:21);
5'-$A_sG_s^{Me}C_sa_st_st_sg_sg_st_sa_st_sT^{Me}C_sA$-3' (SEQ ID NO:22);
5'-$A_sG_s^{Me}C_sa_st_st_sg_sg_st_sa_st_sT_s^{Me}CA$-3' (SEQ ID NO:23);
5'-$AG_s^{Me}C_sa_st_st_sg_sg_st_sa_st_sT_s^{Me}CA$-3' (SEQ ID NO:24);
5'-$AG^{Me}C_sa_st_st_sg_sg_st_sa_st_sT^{Me}CA$-3' (SEQ ID NO:25);
5'-$G_s^{Me}C_sa_st_st_sg_sg_st_sa_st_sT_s^{Me}C_sA$-3' (SEQ ID NO:26);
5'-$G^{Me}C_sa_st_st_sg_sg_st_sa_st_sT_s^{Me}C_sA$-3' (SEQ ID NO:27);
5'-$G_s^{Me}Ca_st_st_sg_sg_st_sa_st_sT_s^{Me}C_sA$-3' (SEQ ID NO:28);
5'-$G_s^{Me}C_sa_st_st_sg_sg_st_sa_stT_s^{Me}C_sA$-3' (SEQ ID NO:29);
5'-$G_s^{Me}C_sa_st_st_sg_sg_st_sa_st_sT^{Me}C_sA$-3' (SEQ ID NO:30);
5'-$G_s^{Me}C_sa_st_st_sg_sg_st_sa_st_sT_s^{Me}CA$-3' (SEQ ID NO:31);
5'-$G_s^{Me}C_sa_st_st_sg_sg_st_sa_st_sT_s^{Me}CA$-3' (SEQ ID NO:32);
5'-$G^{Me}C_sa_st_st_sg_sg_st_sa_st_sT^{Me}CA$-3' (SEQ ID NO:33);
5'-$G_s^{Me}C_sa_st_st_sg_sg_st_sa_st_sT_s^{Me}C$-3' (SEQ ID NO:34);
5'-$G^{Me}C_sa_st_st_sg_sg_st_sa_st_sT_s^{Me}C$-3' (SEQ ID NO:35);
5'-$G_s^{Me}Ca_st_st_sg_sg_st_sa_st_sT_s^{Me}C$-3' (SEQ ID NO:36);
5'-$G_s^{Me}C_sa_st_st_sg_sg_st_sa_stT_s^{Me}C$-3' (SEQ ID NO:37);
5'-$G_s^{Me}C_sa_st_st_sg_sg_st_sa_st_sT^{Me}C$-3' (SEQ ID NO:38);
5'-$G^{Me}C_sa_st_st_sg_sg_st_sa_st_sT^{Me}C$-3' (SEQ ID NO:39); and
5'-$G^{Me}Ca_st_st_sg_sg_st_sa_stT^{Me}C$-3' (SEQ ID NO:40), wherein the capital letters represent locked nucleic acid (LNA) monomers, lowercase letters represent DNA monomers, internucleoside linkages are phosphorthioate where indicated by the subscript s or phosphodiester as indicated by the lack of the subscript s, and superscript Me indicates that LNA C have a 5-methyl group.

9. The compound of claim 1 wherein all of the nucleotide analogues are locked nucleic acids (LNA).

10. The compound of claim 9 wherein all of the internucleobase linkage groups between the nucleobase units of the nucleobase sequence are phosphorothioate linkage groups.

11. A conjugate comprising the compound according to any of claims 1, 2, 3, 7, 8, 9 and 10 and at least one non-nucleotide or non-polynucleotide moiety covalently attached to said compound.

12. A pharmaceutical composition comprising the compound according to any of claims 1, 2, 5, 3, 8, 9 and 10 and a pharmaceutically acceptable diluent, carrier or adjuvant.

13. A method of treating a disease or condition characterized by abnormal levels of apolipoprotein B100 (Apo-B100) comprising administering to a subject in need thereof an effective amount of the compound according to any of claims 1, 2, 3, 7, 8, 9 and 10.

14. The method of claim 13, wherein the disease or condition is selected from the group consisting of: atherosclerosis, hypercholesterolemia and hyperlipidemia.

15. The compound of claim 1, wherein said compound comprises at least 3 nucleotide analogues.

16. The compound of claim 2, wherein the nucleotides in region B are DNA nucleotides.

17. The compound of claim 2, further comprising one or two nucleotides (region D), wherein the nucleobase sequence comprises, in a 5' to 3' direction: region D, followed by region A, followed by region B, followed by region C.

18. A pharmaceutical composition comprising the conjugate of claim 11, and a pharmaceutically acceptable diluent, carrier, or adjuvant.

19. A method of treating a disease or condition characterized by abnormal levels of apolipoprotein B100 (Apo-B100) comprising administering to a subject an effective amount of the conjugate of claim 11.

20. The method of claim 19, wherein the disease or condition is selected from the group consisting of: atherosclerosis, hypercholesterolemia, and hyperlipidemia.

21. The oligomeric compound 5'-$G_s{}^{Me}C_s a_s a_s t_s t_s g_s g_s t_s a_s t_s T_s{}^{Me}C_s A$-3' (SEQ ID NO:26), wherein the capital letters represent beta-D-oxy-LNA monomers, lowercase letters represent DNA monomers, all internucleoside linkages are phosphorthioate, as indicated by the subscript s, and superscript Me indicates that the beta-D-oxy-LNA C have a 5-methyl group.

22. A conjugate comprising the compound according to claim 21 and at least one non-nucleotide or non-polynucleotide moiety covalently attached to the compound.

23. A pharmaceutical composition comprising the compound according to claim 21 and a pharmaceutically acceptable diluent, carrier or adjuvant.

24. A pharmaceutical composition comprising the conjugate according to claim 22 and a pharmaceutically acceptable diluent, carrier or adjuvant.

25. A method of treating a disease or condition characterized by abnormal levels of apolipoprotein B100 (Apo-B100) comprising administering to a subject in need thereof an effective amount of the compound according to claim 21.

26. The method of claim 25, wherein the disease or condition is selected from the group consisting of: atherosclerosis, hypercholesterolemia and hyperlipidemia.

27. A method of treating a disease or condition characterized by abnormal levels of apolipoprotein B100 (Apo-B100) comprising administering to a subject in need thereof an effective amount of the conjugate according to claim 22.

28. The method of claim 27, wherein the disease or condition is selected from the group consisting of: atherosclerosis, hypercholesterolemia and hyperlipidemia.

* * * * *

UNITED STATES PATENT AND TRADEMARK OFFICE
CERTIFICATE OF CORRECTION

PATENT NO. : 8,470,791 B2
APPLICATION NO. : 12/532275
DATED : June 25, 2013
INVENTOR(S) : Henrik Frydenlund Hansen It is certified that error appears in the above-identified patent and that said Letters Patent is hereby corrected as shown below:

Title Page 2, item (56), Col. 1 (Other Publications), line 43, delete "antissense" and insert
-- antisense --

Title Page 2, item (56), Col. 2 (Other Publications), line 1, delete "antisesnse" and insert
-- antisense --

Title Page 2, item (56), Col. 2 (Other Publications), line 35, delete "et aL," and insert
-- et al, --

Title Page 2, item (56), Col. 2 (Other Publications), line 56, delete "et aL," and insert
-- et al, --

Title Page 3, item (56), Col. 2 (Other Publications), line 28, delete "Depedent" and insert
-- Dependent --

Title Page 3, item (56), Col. 2 (Other Publications), line 51, delete "Hepatisis" and insert
-- Hepatitis --

Signed and Sealed this
Eighth Day of October, 2013

Teresa Stanek Rea
*Deputy Director of the United States Patent and Trademark Office*

SEQUENCE LISTING

```
<160> NUMBER OF SEQ ID NOS: 49

<210> SEQ ID NO 1
<211> LENGTH: 16
<212> TYPE: DNA
<213> ORGANISM: Artificial Sequence
<220> FEATURE:
<223> OTHER INFORMATION: Antisense motif

<400> SEQUENCE: 1
cagcattggt attcag                                                    16

<210> SEQ ID NO 2
<211> LENGTH: 15
<212> TYPE: DNA
<213> ORGANISM: Artificial Sequence
<220> FEATURE:
<223> OTHER INFORMATION: Antisense motif

<400> SEQUENCE: 2
cagcattggt attca                                                     15

<210> SEQ ID NO 3
<211> LENGTH: 15
<212> TYPE: DNA
<213> ORGANISM: Artificial Sequence
<220> FEATURE:
```

<223> OTHER INFORMATION: Antisense motif

<400> SEQUENCE: 3
agcattggta ttcag                                                          15

<210> SEQ ID NO 4
<211> LENGTH: 14
<212> TYPE: DNA
<213> ORGANISM: Artificial Sequence
<220> FEATURE:
<223> OTHER INFORMATION: Antisense motif

<400> SEQUENCE: 4
cagcattggt attc                                                           14

<210> SEQ ID NO 5
<211> LENGTH: 14
<212> TYPE: DNA
<213> ORGANISM: Artificial Sequence
<220> FEATURE:
<223> OTHER INFORMATION: Antisense motif

<400> SEQUENCE: 5
agcattggta ttca                                                           14

<210> SEQ ID NO 6
<211> LENGTH: 14
<212> TYPE: DNA
<213> ORGANISM: Artificial Sequence
<220> FEATURE:
<223> OTHER INFORMATION: Antisense motif

<400> SEQUENCE: 6
gcattggtat tcag                                                           14

<210> SEQ ID NO 7
<211> LENGTH: 13
<212> TYPE: DNA
<213> ORGANISM: Artificial Sequence
<220> FEATURE:
<223> OTHER INFORMATION: Antisense motif

<400> SEQUENCE: 7
cagcattggt att                                                            13

<210> SEQ ID NO 8
<211> LENGTH: 13
<212> TYPE: DNA
<213> ORGANISM: Artificial Sequence
<220> FEATURE:
<223> OTHER INFORMATION: Antisense motif

<400> SEQUENCE: 8
agcattggta ttc                                                            13

<210> SEQ ID NO 9
<211> LENGTH: 13
<212> TYPE: DNA
<213> ORGANISM: Artificial Sequence
<220> FEATURE:
<223> OTHER INFORMATION: Antisense motif

<400> SEQUENCE: 9
gcattggtat tca                                                            13

<210> SEQ ID NO 10

```
<211> LENGTH: 13
<212> TYPE: DNA
<213> ORGANISM: Artificial Sequence
<220> FEATURE:
<223> OTHER INFORMATION: Antisense motif

<400> SEQUENCE: 10
cattggtatt cag                                                            13

<210> SEQ ID NO 11
<211> LENGTH: 12
<212> TYPE: DNA
<213> ORGANISM: Artificial Sequence
<220> FEATURE:
<223> OTHER INFORMATION: Antisense motif

<400> SEQUENCE: 11
cagcattggt at                                                             12

<210> SEQ ID NO 12
<211> LENGTH: 12
<212> TYPE: DNA
<213> ORGANISM: Artificial Sequence
<220> FEATURE:
<223> OTHER INFORMATION: Antisense motif

<400> SEQUENCE: 12
agcattggta tt                                                             12

<210> SEQ ID NO 13
<211> LENGTH: 12
<212> TYPE: DNA
<213> ORGANISM: Artificial Sequence
<220> FEATURE:
<223> OTHER INFORMATION: Antisense motif

<400> SEQUENCE: 13
gcattggtat tc                                                             12

<210> SEQ ID NO 14
<211> LENGTH: 12
<212> TYPE: DNA
<213> ORGANISM: Artificial Sequence
<220> FEATURE:
<223> OTHER INFORMATION: Antisense motif

<400> SEQUENCE: 14
cattggtatt ca                                                             12

<210> SEQ ID NO 15
<211> LENGTH: 12
<212> TYPE: DNA
<213> ORGANISM: Artificial Sequence
<220> FEATURE:
<223> OTHER INFORMATION: Antisense motif

<400> SEQUENCE: 15
attggtattc ag                                                             12

<210> SEQ ID NO 16
<211> LENGTH: 15
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(15)
```

<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (13)..(15)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 16
agcattggta ttcag                                                        15

<210> SEQ ID NO 17
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 17
agcattggta ttca                                                         14

<210> SEQ ID NO 18
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (2)..(14)
<223> OTHER INFORMATION: Phosphorothioate linkages
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)

```
<223> OTHER INFORMATION: 5 methyl cytosine

<400> SEQUENCE: 18
agcattggta ttca                                                              14

<210> SEQ ID NO 19
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(14)
<223> OTHER INFORMATION: Phosphorothioate linkage
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 19
agcattggta ttca                                                              14

<210> SEQ ID NO 20
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(3)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (4)..(14)
<223> OTHER INFORMATION: Phosphorothioate linkages
<220> FEATURE:
<221> NAME/KEY: misc_feature
<222> LOCATION: (12)..(14)
<223> OTHER INFORMATION: LNA units

<400> SEQUENCE: 20
agcattggta ttca                                                              14

<210> SEQ ID NO 21
<211> LENGTH: 14
<212> TYPE: DNA
<213> ORGANISM: Artificial Sequence
<220> FEATURE:
```

```
<223> OTHER INFORMATION: LNA oligomeric compound
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 21
agcattggta ttca                                                        14

<210> SEQ ID NO 22
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(14)
<223> OTHER INFORMATION: Phosphorothioate linkages
<220> FEATURE:
<221> NAME/KEY: misc_feature
<222> LOCATION: (13)..(13)
<223> OTHER INFORMATION: 5 methyl cytosine

<400> SEQUENCE: 22
agcattggta ttca                                                        14

<210> SEQ ID NO 23
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(3)
```

```
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(14)
<223> OTHER INFORMATION: Phosphorothioate linkages
<220> FEATURE:
<221> NAME/KEY: misc_feature
<222> LOCATION: (13)..(13)
<223> OTHER INFORMATION: 5 methyl cytosine

<400> SEQUENCE: 23
agcattggta ttca                                                        14

<210> SEQ ID NO 24
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (2)..(13)
<223> OTHER INFORMATION: Phosphorothioate linkages
<220> FEATURE:
<221> NAME/KEY: misc_feature
<222> LOCATION: (3)..(3)
<223> OTHER INFORMATION: 5 mthyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 24
agcattggta ttca                                                        14

<210> SEQ ID NO 25
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(3)
<223> OTHER INFORMATION: LNA units
<220> FEATURE:
<221> NAME/KEY: misc_feature
<222> LOCATION: (3)..(12)
<223> OTHER INFORMATION: Phosphorothioate linkages
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (12)..(14)
<223> OTHER INFORMATION: LNA units
<220> FEATURE:
<221> NAME/KEY: misc_feature
<222> LOCATION: (13)..(13)
<223> OTHER INFORMATION: 5 methyl cytosine

<400> SEQUENCE: 25
```

-continued agcattggta ttca                                                          14

<210> SEQ ID NO 26
<211> LENGTH: 13
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 26
gcattggtat tca                                                           13

<210> SEQ ID NO 27
<211> LENGTH: 13
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(13)
<223> OTHER INFORMATION: Phosphorothioate linkage
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 27
gcattggtat tca                                                           13

<210> SEQ ID NO 28
<211> LENGTH: 13
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (1)..(2)

```
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (3)..(13)
<223> OTHER INFORMATION: Phosphorothioate linkage
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 28
gcattggtat tca                                                        13

<210> SEQ ID NO 29
<211> LENGTH: 13
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(13)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 29
gcattggtat tca                                                        13

<210> SEQ ID NO 30
<211> LENGTH: 13
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(11)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(13)
```

```
<223> OTHER INFORMATION: Phosphorothioate linkage
<220> FEATURE:
<221> NAME/KEY: misc_feature
<222> LOCATION: (12)..(12)
<223> OTHER INFORMATION: 5 methyl cytosine

<400> SEQUENCE: 30
gcattggtat tca                                                        13

<210> SEQ ID NO 31
<211> LENGTH: 13
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 31
gcattggtat tca                                                        13

<210> SEQ ID NO 32
<211> LENGTH: 13
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(12)
<223> OTHER INFORMATION: Phosphorothioate linkages
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (12)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 32
gcattggtat tca                                                        13

<210> SEQ ID NO 33
<211> LENGTH: 12
<212> TYPE: DNA
<213> ORGANISM: Artificial Sequence
<220> FEATURE:
```

```
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(11)
<223> OTHER INFORMATION: Phosphorothioate linkages
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(13)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 33
gcattggtat tc                                                          12

<210> SEQ ID NO 34
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methl cytosine
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methl cytosine

<400> SEQUENCE: 34
gcattggtat tc                                                          12

<210> SEQ ID NO 35
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(11)
<223> OTHER INFORMATION: Phosphorothioate linkages
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(12)
```

```
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 35
gcattggtat tc                                                              12

<210> SEQ ID NO 36
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (3)..(12)
<223> OTHER INFORMATION: Phosphorothioate linkages
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 36
gcattggtat tc                                                              12

<210> SEQ ID NO 37
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 37
gcattggtat tc                                                              12

<210> SEQ ID NO 38
```

```
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(11)
<223> OTHER INFORMATION: Phosphorothioate linkages
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 38
gcattggtat tc                                                         12

<210> SEQ ID NO 39
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(11)
<223> OTHER INFORMATION: Phosphorothioate linkages
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 39
gcattggtat tc                                                         12

<210> SEQ ID NO 40
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(2)
<223> OTHER INFORMATION: LNA units
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (3)..(10)
```

```
<223> OTHER INFORMATION: Phosphorothioate linkages
<220> FEATURE:
<221> NAME/KEY: misc_feature
<222> LOCATION: (11)..(12)
<223> OTHER INFORMATION: LNA units
<220> FEATURE:
<221> NAME/KEY: misc_feature
<222> LOCATION: (12)..(12)
<223> OTHER INFORMATION: 5 methyl cytosine

<400> SEQUENCE: 40
gcattggtat tc                                                           12

<210> SEQ ID NO 41
<211> LENGTH: 15
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(15)
<223> OTHER INFORMATION: Phosphorothioate linkages
<220> FEATURE:
<221> NAME/KEY: misc_feature
<222> LOCATION: (1)..(3)
<223> OTHER INFORMATION: Oxy-LNA
<220> FEATURE:
<221> NAME/KEY: misc_feature
<222> LOCATION: (1)..(1)
<223> OTHER INFORMATION: 5 methyl cytosine
<220> FEATURE:
<221> NAME/KEY: misc_feature
<222> LOCATION: (13)..(15)
<223> OTHER INFORMATION: LNA
<220> FEATURE:
<221> NAME/KEY: misc_feature
<222> LOCATION: (14)..(14)
<223> OTHER INFORMATION: 5 methyl cytosine

<400> SEQUENCE: 41
cagcattggt attca                                                        15

<210> SEQ ID NO 42
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (12)..(13)
<223> OTHER INFORMATION: LNA
<220> FEATURE:
<221> NAME/KEY: misc_feature
<222> LOCATION: (13)..(13)
<223> OTHER INFORMATION: 5 methyl cytosine

<400> SEQUENCE: 42
agcattggta ttca                                                         14

<210> SEQ ID NO 43
<211> LENGTH: 14
<212> TYPE: DNA
<213> ORGANISM: Artificial Sequence
<220> FEATURE:
```

```
<223> OTHER INFORMATION: LNA oligomeric compound
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (13)..(13)
<223> OTHER INFORMATION: 5 methyl cytosine

<400> SEQUENCE: 43
agcattggta ttca                                                      14

<210> SEQ ID NO 44
<211> LENGTH: 14
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(14)
<223> OTHER INFORMATION: Phosphorothioate linkages
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (3)..(3)
<223> OTHER INFORMATION: 5 methyl cytosine
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (13)..(13)
<223> OTHER INFORMATION: 5 methyl cytosine

<400> SEQUENCE: 44
agcattggta ttca                                                      14

<210> SEQ ID NO 45
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (11)..(12)
<223> OTHER INFORMATION: LNA
<220> FEATURE:
<221> NAME/KEY: misc_feature
<222> LOCATION: (12)..(12)
<223> OTHER INFORMATION: 5 methyl cytosine

<400> SEQUENCE: 45
```

```
gcattggtat tc                                                              12
```

<210> SEQ ID NO 46
<211> LENGTH: 12
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(12)
<223> OTHER INFORMATION: Phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (10)..(2)
<223> OTHER INFORMATION: LNA
<220> FEATURE:
<221> NAME/KEY: misc_feature
<222> LOCATION: (12)..(12)
<223> OTHER INFORMATION: 5 methyl cytosine

<400> SEQUENCE: 46

```
gcattggtat tc                                                              12
```

<210> SEQ ID NO 47
<211> LENGTH: 10
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(10)
<223> OTHER INFORMATION: Phosphorothioate linkages
<220> FEATURE:
<221> NAME/KEY: misc_feature
<222> LOCATION: (1)..(1)
<223> OTHER INFORMATION: LNA
<220> FEATURE:
<221> NAME/KEY: misc_feature
<222> LOCATION: (10)..(10)
<223> OTHER INFORMATION: LNA

<400> SEQUENCE: 47

```
gcattggtat                                                                 10
```

<210> SEQ ID NO 48
<211> LENGTH: 10
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(10)
<223> OTHER INFORMATION: Phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (9)..(10)

```
<223> OTHER INFORMATION: LNA

<400> SEQUENCE: 48
gcattggtat                                                          10

<210> SEQ ID NO 49
<211> LENGTH: 10
<212> TYPE: DNA
<213> ORGANISM: Artificial Sequence
<220> FEATURE:
<223> OTHER INFORMATION: LNA oligomeric compound
<220> FEATURE:
<221> NAME/KEY: misc_feature
<222> LOCATION: (1)..(10)
<223> OTHER INFORMATION: Phosphorothioate linkages
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (2)..(2)
<223> OTHER INFORMATION: 5 methyl cytosine
<220> FEATURE:
<221> NAME/KEY: misc_feature
<222> LOCATION: (8)..(10)
<223> OTHER INFORMATION: LNA

<400> SEQUENCE: 49
gcattggtat                                                          10
```